US010583309B2

(12) United States Patent
Deisseroth et al.

(10) Patent No.: US 10,583,309 B2
(45) Date of Patent: Mar. 10, 2020

(54) MATERIALS AND APPROACHES FOR OPTICAL STIMULATION OF THE PERIPHERAL NERVOUS SYSTEM

(71) Applicant: The Board of Trustees of the Leland Stanford Junior University, Stanford, CA (US)

(72) Inventors: Karl A. Deisseroth, Stanford, CA (US); Scott L. Delp, Stanford, CA (US); Michael E. Llewellyn, Menlo Park, CA (US); Christine A. McLeavey Payne, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/351,067

(22) Filed: Nov. 14, 2016

(65) Prior Publication Data
US 2017/0072219 A1 Mar. 16, 2017

Related U.S. Application Data

(62) Division of application No. 14/265,013, filed on Apr. 29, 2014, now abandoned, which is a division of
(Continued)

(51) Int. Cl.
*A61N 5/06* (2006.01)
(52) U.S. Cl.
CPC ......... *A61N 5/0622* (2013.01); *A61N 5/0601* (2013.01); *A61N 5/0613* (2013.01);
(Continued)
(58) Field of Classification Search
CPC ............................. A61N 5/062; A61N 5/0622
See application file for complete search history.

(56) References Cited

U.S. PATENT DOCUMENTS 2,968,302 A 1/1961 Fry et al.
3,131,690 A 5/1964 Innis et al.
(Continued)

FOREIGN PATENT DOCUMENTS

CN 1079464 A 12/1993
CN 1558222 A 12/2004
(Continued)

OTHER PUBLICATIONS

Han X, Boyden ES (2007) Multiple-Color Optical Activation, Silencing, and Desynchronization of Neural Activity, with Single-Spike Temporal Resolution. PLoS ONE 2(3): e299. doi:10.1371/journal.pone.0000299. Available at http://journals.plos.org/plosone/article/file?id=10.1371/journal.pone.0000299&type=printable.*
(Continued)

*Primary Examiner* — John R Downey
(74) *Attorney, Agent, or Firm* — Rudy J. Ng; Paula A. Borden; Bozicevic, Field & Francis LLP

(57) ABSTRACT

A variety of methods, devices, systems and arrangements are implemented for stimulation of the peripheral nervous system. Consistent with one embodiment of the present invention, method is implemented in which light-responsive channels or pumps are engineered in a set of motor units that includes motor units of differing physical volumes. Optical stimuli are also provided to the light-responsive channels or pumps at an optical intensity that is a function of the size of motor units to be recruited. In certain implementations, the intensity of the optical stimuli is increased so as to recruit increasingly larger motor units.

16 Claims, 10 Drawing Sheets

Related U.S. Application Data application No. 12/996,753, filed as application No. PCT/US2009/049936 on Jul. 8, 2009, now Pat. No. 9,101,759.

(60) Provisional application No. 61/079,035, filed on Jul. 8, 2008.

(52) U.S. Cl.
CPC ............... *A61N 2005/0626* (2013.01); *A61N 2005/0652* (2013.01)

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,308,392 B2 | 4/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,360,472 B2 | 6/2016 | Deisseroth et al. |
| 9,365,628 B2 | 6/2016 | Deisseroth et al. |
| 9,394,347 B2 | 7/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |

(56) References Cited

U.S. PATENT DOCUMENTS

| | | |
|---|---|---|
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1* | 3/2007 | Boyden ............... A61K 31/137 424/718 |
| 2007/0054319 A1 | 3/2007 | Boyden et al. |
| 2007/0060915 A1 | 3/2007 | Kucklick |
| 2007/0060984 A1* | 3/2007 | Webb .................. A61N 5/0601 607/89 |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |

(56) References Cited

U.S. PATENT DOCUMENTS

| | | |
|---|---|---|
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0224095 A1 | 9/2011 | Zoller et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096036 A1 | 4/2016 | Deisseroth et al. |
| 2016/0175607 A1 | 6/2016 | Deisseroth et al. |
| 2016/0194624 A1 | 7/2016 | Deisseroth et al. |
| 2016/0199663 A1 | 7/2016 | Deisseroth et al. |
| 2016/0222073 A1 | 8/2016 | Deisseroth et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Definition of Implant; Merriam-Webster Dictionary; retrieved Nov. 7, 2016 (http://www.merriam-webster.com/dictionary/implant).

Ferenczi, et al.; "Optogenetic approaches addressing extracellular modulation of neural excitability"; Scientific Reports; vol. 6, 20 pages (Apr. 5, 2016).

Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).

Shimizu, et al.; "NMDA Receptor-Dependent Synaptic Reinforcement as a Crucial Process for Memory Consolidation"; Science; vol. 290, pp. 1170-1174 (Nov. 10, 2000).

Zeng, et al.; "Activation of acid-sensing ion channels by localized proton transient reveals their role in proton signaling"; Scientific Reports; vol. 5, 14 pages (Sep. 15, 2015).

Zeng, et al.; "Proton production, regulation and pathophysiological roles in the mammalian brain"; Neuroscience Bulletin; vol. 28, No. 1, pp. 1-13 (Feb. 1, 2012).

Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).

Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

Co-pending U.S. Appl. No. 15/334,007, filed Oct. 25, 2016.
Co-pending U.S. Appl. No. 15/008,214, filed Jan. 27, 2016.
Co-pending U.S. Appl. No. 15/059,159, filed Mar. 2, 2016.
Co-pending U.S. Appl. No. 15/095,519, filed Apr. 11, 2016.

(56) References Cited

OTHER PUBLICATIONS

Co-pending U.S. Appl. No. 15/147,772, filed May 5, 2016.
Co-pending U.S. Appl. No. 15/153,299, filed May 12, 2016.
Co-pending U.S. Appl. No. 15/153,305, filed May 12, 2016.
Co-pending U.S. Appl. No. 15/156,124, filed May 16, 2016.
Co-pending U.S. Appl. No. 15/194,379, filed Jun. 27, 2016.
Co-pending U.S. Appl. No. 15/214,399, filed Jul. 19, 2016.
Co-pending U.S. Appl. No. 15/214,400, filed Jul. 19, 2016.
Co-pending U.S. Appl. No. 15/214,402, filed Jul. 19, 2016.
Co-pending U.S. Appl. No. 15/214,403, filed Jul. 19, 2016.
Co-pending U.S. Appl. No. 15/229,064, filed Aug. 4, 2016.
Co-pending U.S. Appl. No. 15/126,859, filed Sep. 16, 2016.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila* rhodopsin cytoplasmic tail domain is required for maintenance of rhabdomere structure." The FASEB Journal, 2007, vol. 21, p. 449-455.
Airan, et al.; "Integration of light-controlled neuronal firing and fast circuit imaging"; Current Opinion in Neurobiology; vol. 17, pp. 587-592 (2007).
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.

Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Post-synaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).

(56) References Cited

OTHER PUBLICATIONS

Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow, et al.; "High-performance genetically targetable optical neural silencing by light-driven proton pumps"; Nature; vol. 463, pp. 98-102 (Jan. 7, 2010).
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. , 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.

Davidson, et al.; "Viral Vectors for Gene Delivery to the Nervous System"; Nature Reviews Neuroscience; vol. 4, pp. 353-364 (May 2003).
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.

(56) References Cited

OTHER PUBLICATIONS

Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain", Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Fanselow, et al.; "Why We Think Plasticity Underlying Pavlovian Fear Conditioning Occurs in the Basolateral Amygdala"; Neuron; vol. 23, pp. 229-232 (Jun. 1999).
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from Bacillus subtilis DNA" Gene, 1984, vol. 32(1-2): pp. 11-20.
Glick et al."Factors affecting the expression of foreign proteins in Escherichia coli", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gong, et al.; "Enhanced Archaerhodopsin Fluorescent Protein Voltage Indicators"; PLOS One; vol. 8, Issue 6, 10 pages (Jun. 2013).
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for Streptomyces phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.

(56) References Cited

OTHER PUBLICATIONS

Hammer et al., "Spontaneous inflammatory disease in transgenic rats expressing HLA-B27 and Human β₂m: an animal model of HLA-B27-associated human disorders", Cell, 1990, vol. 63, pp. 1099-1112.
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Jones, et al.; "Animal Models of Schizophrenia"; British Journal of Pharmacology; vol. 164, pp. 1162-1194 (2011).
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.

(56) References Cited

OTHER PUBLICATIONS

Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-1 0.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Bioi. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.

(56) References Cited

OTHER PUBLICATIONS

Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E—Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 1 .I-9.1 1 .I 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.

(56) References Cited

OTHER PUBLICATIONS

Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+—Cl-cotransporter KCC2 and Impairs Neuronal Cl— Extrusion", The Journal of Cell Biology, 2002, vol. 159: pp. 747-752.
Rogers, et al.; "Effects of ventral and dorsal CA1 subregional lesions on trace fear conditioning"; Neurobiology of Learning and Memory; vol. 86, pp. 72-81 (2006).
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin", Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.

(56) References Cited

OTHER PUBLICATIONS

Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.

Van Der Linden, "Functional brain imaging and pharmacotherapy in social phobia: single photon emission computed tomography before and after Treatment with the selective serotonin reuptake inhibitor citalopram," Prog Neuro-psychopharmacol Biot Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to

(56) References Cited

OTHER PUBLICATIONS stimulation of the amygdala and hypothalamus in conscious cats"; Folia Pharmacol. Japon; vol. 83, No. 3, pp. 237-248 (Mar. 1984). [English abstract translation].

Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].

Yamazoe, et al. "Efficient generation of dopaminergic neurons from mouse embryonic stem cells enclosed in hollow fibers", Biomaterials, 2006, vol. 27, pp. 4871-4880.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Yizhar et al., "Optogenetics in neural systems", Neuron Primer, vol. 71, No. 1, pp. 9-34 (Jul. 14, 2011).

Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang "Multimodal fast optical interrogation of neural circuitry," Nature, 2007, vol. 446, pp. 633-641.

Zhang, et al. "Channelrhodopsin-2 and optical control of excitable cells," Nature Methods,2006, vol. 3, No. 10, pp. 785-792.

Zhang, et al. "Red-Shifted Optogenetic Excitation: a Tool for Fast Neural Control Derived from *Volvox carteri*", Nature Neurosciences, 2008,vol. 11, No. 6, pp. 631-633.

Zhang, et al., "The Microbial Opsin Family of Optogenetic Tools", Cell, 2011, vol. 147, No. 7, pp. 1146-1457.

Zhang, et al.; "Optogenetic interrogation of neural circuits: Technology for probing mammalian brain structures"; Nature Protocols; vol. 5, No. 3, pp. 439-456 (Feb. 18, 2010).

Zhao, et al., "Improved Expression of Halorhodopsin for Light-Induced Silencing of Neuronal Activity", Brain Cell Biology, 2008, vol. 36 (1-4), pp. 141-154.

Zrenner, E., "Will Retinal Implants Restore Vision?" Science, 2002, vol. 295, No. 5557, pp. 1022-1025.

Zufferey, et al. "Self-Inactivating Lentivirus Vector for Safe and Efficient In Vivo Gene Delivery", Journal of Virology, 1998, vol. 72, No. 12, pp. 9873-9880.

Lin, et al.; "Study of the Circuitry of Nucleus Accumbens and its Effect on Addiction by Optogenetic Methods: 964"; Neurosurgery; vol. 67, No. 2, pp. 557 (Aug. 2010).

Tsuchida; "Nervous Control of Micturition"; The Japanese Journal of Urology; vol. 80, No. 9, pp. 1257-1277 (1989).

Bibel, et al.; "Differentiation of mouse embryonic stem cells into a defined neuronal lineage"; Nature Neuroscience; vol. 7, No. 9, pp. 1033-1009 (Sep. 2004).

Daniel, et al.; "Stress Modulation of Opposing Circuits in the Bed Nucleus of the Stria Terminalis"; Neuropsychopharmacology Reviews; vol. 41, pp. 103-125 (2016).

Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).

Knopfel, et al.; "Remote control of cells"; Nature Nanotechnology; vol. 5, pp. 560-561 (Aug. 2010).

Steimer; "The biology of fear- and anxiety-related behaviors"; Dialogues in Clinical Neuroscience; vol. 4, No. 3, pp. 231-249 (Sep. 2002).

Stuber; "Dissecting the neural circuitry of addiction and psychiatric disease with optogenetics"; Neuropsychopharmacology; vol. 35, No. 1, pp. 341-342 (2010).

Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).

Sofuoglu, et al.; "Cholinergic Functioning in Stimulant Addiction: Implications for Medications Development"; CNS Drugs; vol. 23, No. 11, pp. 939-952 (Nov. 1, 2009).

Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).

Gerits, et al.; "Optogenetically Induced Behavioral and Functional Network Changes in Primates"; Current Biology; vol. 22, pp. 1722-1726 (Sep. 25, 2012).

Han, et al.; "Optogenetics in the nonhuman primate"; Prog. Brain Res.; vol. 196, pp. 215-233 (2012).

Definition of integral. Merriam-Webster Dictionary, retrieved on Mar. 20, 2017; Retrieved from the internet: <http://www.merriam-webster.com/dictionary/integral>.

Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).

Alilain, et al.; "Light-Induced Rescue of Breathing after Spinal Cord Injury"; The Journal of Neuroscience; vol. 28, No. 46, pp. 11862-11870 (Nov. 12, 2008).

Cardin, et al.; "Targeted optogenetic stimulation and recording of neurons in vivo using cell-type-specific expression of Channelrhodopsin-2"; Nature Protocols; vol. 5, No. 2, pp. 247-254 (2010).

Caro, et al.; "Engineering of an Artificial Light-Modulated Potassium Channel"; PLoS One; vol. 7, Issue 8, e43766 (Aug. 2012).

Coleman, et al.; "Assessing Anxiety in Nonhuman Primates"; Ilar Journal; vol. 55, No. 2, pp. 333-346 (2014).

Hagglund, et al.; "Activation of groups of excitatory neurons in the mammalian spinal cord or hindbrain evokes locomotion"; Nature Neuroscience; vol. 13, No. 2, 8 pages (Feb. 2010).

Kleinlogel, et al.; "A gene-fusion strategy for stoichiometric and co-localized expression of light-gated membrane proteins"; Nature Methods; vol. 8, No. 12, pp. 1083-1091 (Dec. 2011).

Kravitz, et al.; "Regulation of parkinsonian motor behaviours by optogenetic control of basal ganglia circuitry"; Nature; vol. 466, No. 622, 8 pages (Jul. 29, 2010).

Luo, et al.; "Synthetic DNA delivery systems"; Nature Biotechnology; vol. 18, pp. 33-37 (Jan. 2000).

Maestripieri, et al.; "A modest proposal: displacement activities as an indicator of emotions in primates"; Anim. Behav.; vol. 44, pp. 967-979 (1992).

Nelson, et al.; "Non-Human Primates: Model Animals for Developmental Psychopathology"; Neuropsychopharmacology; vol. 34, No. 1, pp. 90-105 (Jan. 2009).

Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).

Uniprot Accession No. P02945, integrated into the database on Jul. 21, 1986.

Azizgolshani, et al.; "Reconstituted plant viral capsids can release genes to mammalian cells"; Virology; vol. 441, No. 1, pp. 12-17 (2013).

Racaniello; "How many viruses on Earth?"; Virology Blog; 6 pages; http://www.virology.ws/2013/09/06/how-many-viruses-on-earth/ (Sep. 6, 2013).

Friedman, et al.; "VTA Dopamine Neuron Bursting is Altered in an Animal Model of Depression and Corrected by Desipramine"; J. Mol. Neurosci.; vol. 34, pp. 201-209 (2008).

Hackmann, et al.; "Static and time-resolved step-scan Fourier transform infrared investigations of the photoreaction of halorhodopsin

(56) References Cited

OTHER PUBLICATIONS from Natronobacterium pharaonis: consequences for models of the anion translocation mechanism"; Biophysical Journal; vol. 81, pp. 394-406 (Jul. 2001).

Weiss, et al.; "Galanin: A Significant Role in Depression?"; Annals New York Academy of Sciences; vol. 863, No. 1, pp. 364-382 (1998).

Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).

Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).

Masaki, et al.; "β2-Adrenergic Receptor Regulation of the Cardiac L-Type Ca2+ Channel Coexpressed in a Fibroblast Cell Line"; Receptor; vol. 5, pp. 219-231 (1996).

Smith, et al.; "Proton binding sites involved in the activation of acid-sensing ion channel ASIC2a"; Neuroscience Letters; vol. 426, pp. 12-17 (2007).

Boyden, et al.; "A history of optogenetics: the development of tools for controlling brain circuits with light"; F1000 Biology Reports; vol. 3, No. 11, 12 pages (May 3, 2011).

Knox, et al.; "Heterologous Expression of *Limulus* Rhodopsin"; The Journal of Biological Chemistry; vol. 278, No. 42, pp. 40493-40502 (Oct. 17, 2003).

Lin, et al.; "Characterization of Engineered Channelrhodopsin Variants with Improved Properties and Kinetics"; Biophysical Journal; vol. 96, No. 5, pp. 1803-1814 (Mar. 2009).

Belzung et al., "Optogenetics to study the circuits of fear- and depresssion-like behaviors: A critical analysis," Pharmacology, Biochemistry and Behavior, 2014, 122: 144-157.

Bernstein & Boyden "Optogenetic tools for analyzing the neural circuits of behavior," Trends Cogn Sci., 2011, 15(12): 592-600.

Ahmad, et al. "Heterplogous expression of bovine rhodopsin in *Drosophila* photoreceptor cells" Invest Ophthalmol Vis Sci. 2006, 3722-3728.

Clare "Targeting Ion Channels for Drug Discovery" Discov Med. 2010 vol. 9 No. 46 pp. 1-6.

Clare "Functional Expression of Ion Channels in Mammalian Systems" Protein Science Encyclopedia A.R. Fersht (Ed.) 2008 pp. 79-109.

Reeves et al., "Structure and function in rhodosin: A tetracycline-inducible system in stable mammalian cell lines for high-level expression of opsin mutants" PNAS, 2002 vol. 99 No. 21 pp. 13413-13418.

Nargeot et al.; Molecular basis of the diversity of calcium channels in cardiovascular tissues European Heart Journal, 1997, Supplemental A, A15-A26.

Erbguth et al. "Bimodal Activation of Different Neuron Classes with Spectrally Red-Shifted Channelrhodopsin Chimera C1V1 in Caenorhabditis elegans," PLOS ONE, 2012, vol. 7 No. 10, pp. e46827/1-9.

Li et al.; "Role of a Helix B Lysine Residue in the Photoactive Site in Channelrhodopsins," Biophysical Journal, 2014, vol. 106, pp. 1607-1617.

Prigge et al.: "Functional Studies of Volvox Channelrhodopsin Chimeras," Biophysical Journal, 2010, vol. 98, No. 3, Suppl. 1, 3694 Poster, 1 page.

Prigge et al.; Color-tuned Channelrhodopsins for Multiwavelength Optogenetics, J. Biol. Chem. 2012, vol. 287, No. 38, pp. 31804-31812.

Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.

Duvarci, et al., "The bed Nucleus of the Stria Terminalis Mediates inter-individual variations in anxiety and fear", J. Neurosci., 29(33) 10357-10361 (2009).

Matsuda "Bed nucleus of stria terminalis (BNST)" Benshi Seishin Igaku (Molecular Psychiatric Medicine), 2009, vol. 9 No. 3, p. 46-49.

Neuropsychopharmacology, 2011, vol. 36 No. Suppl.1, p. S110 (Abstract No. 67).

Neuropsychopharmacology, 2012, vol. 38 No. Suppl.1, p. S48 (Abstract No. 37.2).

Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).

\* cited by examiner

FIG. 5A
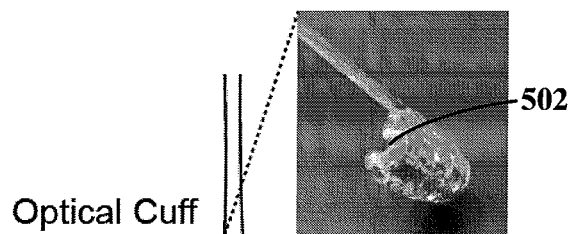
Optical Cuff
FIG. 5C
FIG. 5B
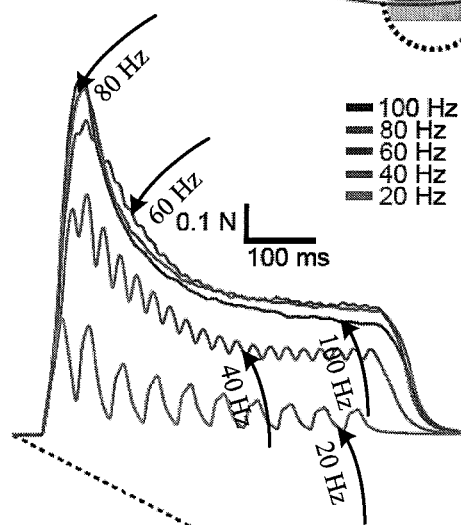
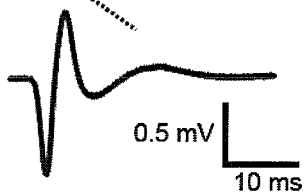
EMG
FIG. 5D
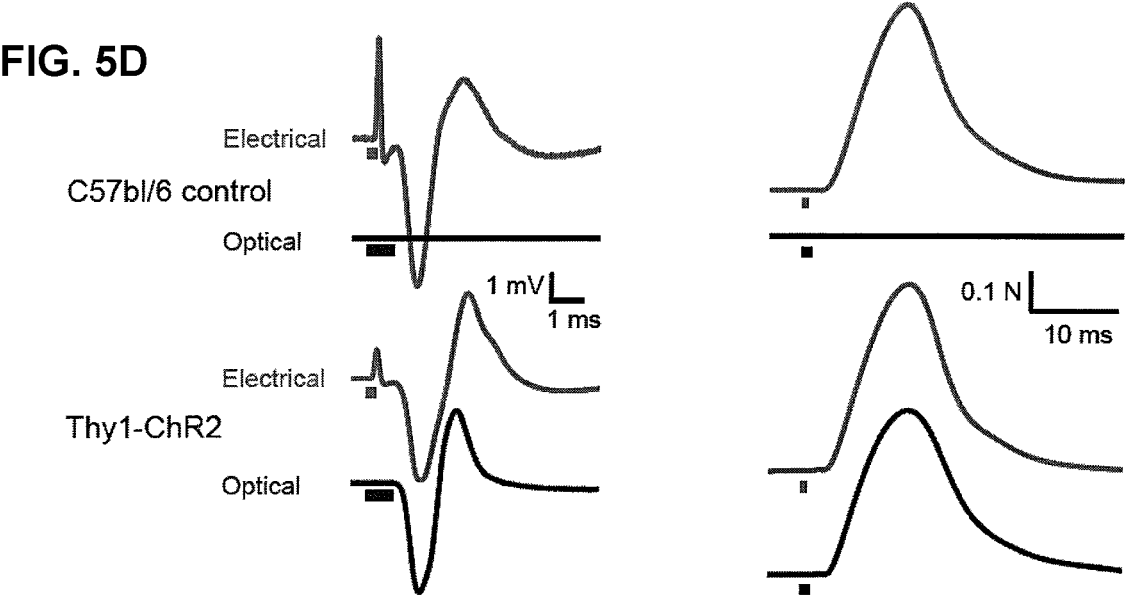

FIG. 7A
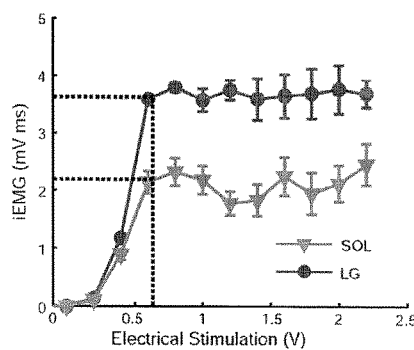
FIG. 7B FIG. 7C FIG. 7D
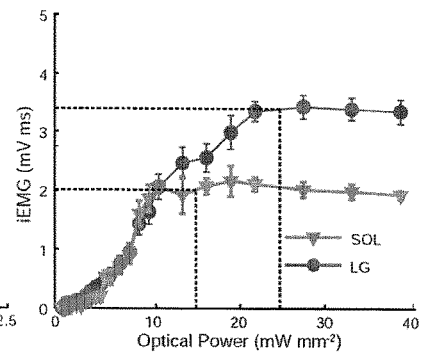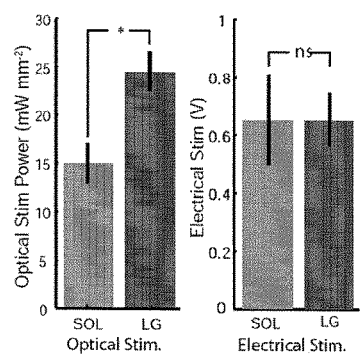
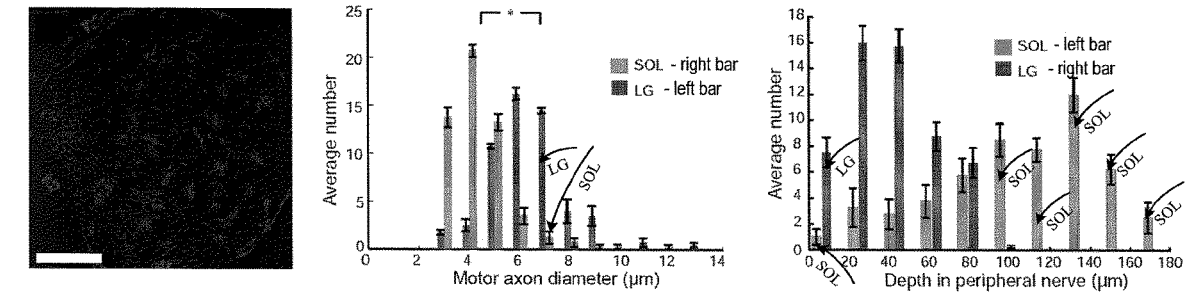
FIG. 7E          FIG. 7F          FIG. 7G

MATERIALS AND APPROACHES FOR OPTICAL STIMULATION OF THE PERIPHERAL NERVOUS SYSTEM

RELATED PATENT DOCUMENTS

This application is a divisional of U.S. patent application Ser. No. 14/265,013, filed Apr. 29, 2014, which is a divisional of U.S. patent application Ser. No. 12/996,753, filed Mar. 10, 2011, now U.S. Pat. No. 9,101,759, which is a national stage filing under 35 U.S.C. § 371 of PCT/US2009/029936, filed Jul. 8, 2009, which claims the benefit, under 35 U.S.C. § 119(e), of U.S. Provisional Patent Application Ser. No. 61/079,035 filed on Jul. 8, 2008, and entitled "Materials and Approaches for Optical Stimulation of the Peripheral Nervous System;" the contents of each of the aforementioned patent applications are incorporated by reference herein in their entireties.

FIELD OF THE INVENTION

The present invention relates generally to stimulation of the peripheral nervous system, and more particularly to arrangements and approaches involving optical stimulus to affect the cells of the peripheral nervous system.

BACKGROUND

The peripheral nervous system extends from the brain and spinal cord to various portions of the body. Two of the main functions of the peripheral nervous system are muscle control and sensory feedback. Peripheral nerves carry signals between the various portions of the body and the central nervous system using electrical signals.

A typical muscle is composed of many thousands of fibers, which contain the contractile machinery of the muscle. Rather than individually controlling each fiber, a single motor neuron can control groups of fibers that form motor units. Motor units vary in size from 100 to several hundred fibers, and also vary in composition of muscle fiber type. Small motor units are typically composed of slow type muscle fibers that are fatigue-resistant, while larger motor units are generally composed of fast type fibers that are easily fatigable and medium sized motor units consist of a mixture of slow and fast fiber types. Motor units are recruited, or turned on, in a specific order that generally begins with the smallest group and progresses to the largest group. In this way, the smaller, fatigue-resistant motor units are used more often, and thus allow for fine force control for longer periods of use. The larger motor units, with larger capacity for generating force, are conserved for brief periods of time when they are most needed, e.g., during a reflex, emergency or other strenuous activities. The size of a motor neuron is correlated to the size of the motor unit that the motor neuron controls, so that a large motor neuron will control a large motor unit.

The normal physiologic recruitment order refers to a typical (healthy) order of motor neuron recruitment, where the size of the motor axons and the motor neuron cell bodies define the sequence of recruitment. For a given synaptic input of current, a smaller motor neuron will be recruited before a larger motor neuron, thus determining the order, small to large.

External electrical stimulation of motor neurons has been attempted. One such attempt stimulates the axon of a motor neuron. This, however, results in a recruitment order that is reversed when compared to the normal physiologic order (the larger motor units are recruited before smaller ones). The implication of this recruitment reversal is that large, fatigable motor units are recruited first, resulting in the loss of fine motor control and sustained motor function. Thus, fatigue has become a limiting factor in limb reanimation projects that have attempted to use electrical stimulation.

The other type main function of the peripheral nervous system, sensory feedback, is responsible for pain, touch, appetite and a variety of other aspects. When problems with arise with sensory feedback mechanisms, the results are often drastic and sometimes even life threatening. For example, chronic pain is a serious health issue that affects many individuals, seriously degrading their quality of life and often having long-term psychological impact. Another issue addressable through sensory feedback relates to appetite suppression.

Aspects of the present invention relate to control and/or stimulation of peripheral nervous system using optical stimulus.

SUMMARY

Aspects of the claimed invention relate generally to stimulation of the peripheral nervous system, and more particularly to arrangements and approaches involving optical stimulus to affect the cells of the peripheral nervous system.

Consistent with an embodiment of the present invention, a method is implemented in which light-responsive channels or pumps are engineered in a set of motor units that includes motor neurons of differing physical volumes. Optical stimuli are also provided to the light-responsive channels or pumps at an optical intensity that is a function of the size of motor units to be recruited. In certain implementations, the intensity of the optical stimuli is increased so as to recruit motor units having increasingly larger motor neurons.

Embodiments of the present invention relate to a method where light-responsive channels or pumps are engineered in a set of peripheral afferent nerves. Optical stimuli are provided to the light-responsive channels or pumps to mitigate pain. Specific implementations relate to the expression of NpHR in the peripheral afferent nerves while providing optical stimuli to modify pain recognition in the central nervous system.

An embodiment of the present invention relates to a method in which light-responsive channels or pumps are engineered in a set of vagal fibers associated with the gastrointestinal system. Optical stimuli are provided to the light-responsive channels or pumps.

Consistent with other embodiments of the present invention, light-responsive channels or pumps are engineered in a set of stem cells. The set of stem cells are implanted at a target location, and optical stimuli are provided to the light-responsive channels or pumps to cause activation of muscle at the target location. Specific embodiments relate to the use of skeletal muscle stem cells to repopulate muscles or implanting the set of stem cells for myocardial repair.

Other embodiments of the present invention relate to a device, kit or system having delivery component for expression of light-responsive channels or pumps in the peripheral nervous system and having an optical component for providing optical stimulus to the light-responsive channels or pumps in the peripheral nervous system. In a particular implementation, the delivery component includes a nucleic acid molecule capable of transporting the light-responsive channels or pumps to which it has been operatively linked.

The above summary of the present invention is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which:

FIG. 5A shows a stimulation cuff for placement around a peripheral nerve, consistent with an embodiment of the present invention;

FIG. 5B shows the muscles electrical response (M-wave) as measured by fine wire electrodes placed in the muscle belly and near the Achilles tendon, consistent with an embodiment of the present invention;

FIG. 5C shows the contractile force output as measured by a force transducer attached to the Achilles tendon, consistent with an embodiment of the present invention;

FIG. 5D depicts electromyography (EMG) and force traces from twitches elicited by optical and electrical stimulations in both Thy1-ChR2 animals and control C57bl/6 animals, consistent with an embodiment of the present invention;

FIG. 7A shows rectified-integrated EMG (iEMG) vs. estimated optical intensity at the surface of the sciatic nerve for soleus (SOL) and lateral gastrocnemius (LG), consistent with an embodiment of the present invention;

FIG. 7B shows rectified-integrated EMG vs. electrical stimulation voltage applied to the sciatic nerve, consistent with an embodiment of the present invention;

FIG. 7C shows optical intensity required to achieve maximum iEMG in SOL and LG, consistent with an embodiment of the present invention;

FIG. 7D shows electrical stimulation required to achieve 95% of maximum iEMG in SOL and LG, consistent with an embodiment of the present invention;

FIG. 7E shows an example cross-section of the sciatic nerve where retrograde dye was injected into the LG only, scale bar=100μ, consistent with an embodiment of the present invention;

FIG. 7F shows distribution of motor axon diameters for SOL and LG found in cross-section of the sciatic nerve, consistent with an embodiment of the present invention;

FIG. 7G shows depth of motor axons for SOL and LG found in cross-section of the sciatic nerve, consistent with an embodiment of the present invention;

Figure 1A:
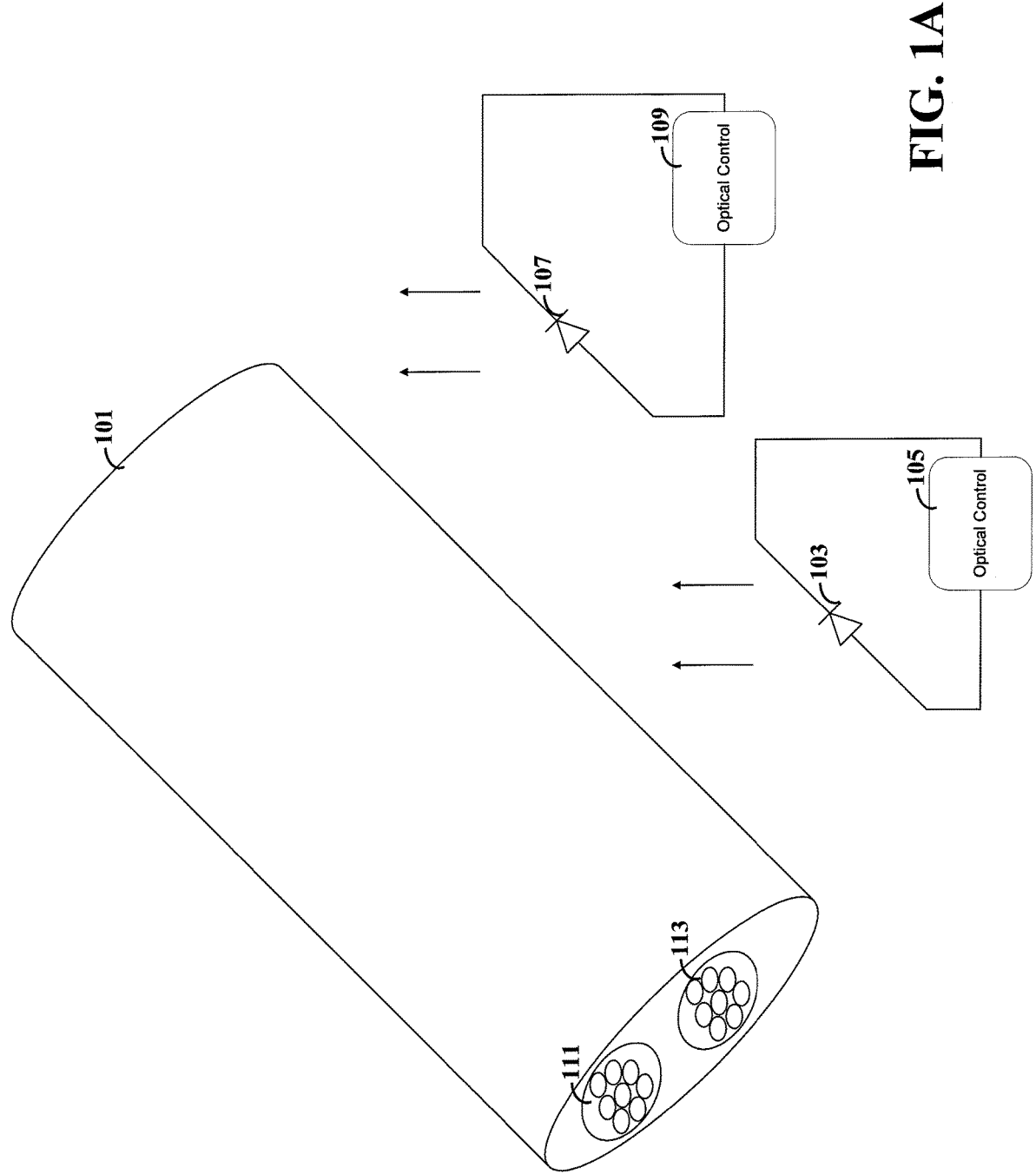
FIG. 1A depicts a peripheral nerve stimulated by optical stimulus devices, consistent with an embodiment of the present invention.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be applicable to a variety of different types of processes, devices and arrangements relating to stimulation of peripheral nerves. While the present invention is not necessarily so limited, various aspects of the invention may be appreciated through a discussion of examples using this context.

According to one embodiment of the present invention, peripheral nerves are optically stimulated to activate light-responsive molecules therein. The light responsive molecules can inhibit and/or facilitate electrical signaling (e.g., action potentials) within the peripheral nerves. For instance, many peripheral nerve bundles include mixed types of nerves (e.g., motor and sensory). One or both of the nerve types can be affected by optical stimulation. In specific instances, each of the nerve types can be selectively stimulated.

As used herein, stimulation can include either activation or deactivation of electrical signaling in the nerves. For instance, nerve cells are stimulated by adjusting the membrane voltage level of the nerve cell to facilitate action potentials or to inhibit action potentials. Moreover, for various embodiments of the present invention, the temporal precision of various light responsive molecules allow for control of individual action potentials, whether the control is via facilitation or inhibition.

According to an embodiment of the present invention, a cuff-shaped optical delivery device allows for stimulation of both types of nerves, or for selective stimulation. These and other implementations can be used for treatment of various conditions, such as muscle spasticity, among other things.

According to an example embodiment of the present invention, motor neurons are optically stimulated. The optical stimulus activates ion channels and/or pumps in the motor neurons to excite or inhibit neural activation and thereby affect contractions and/or relaxation of muscle tissue. Properties of light stimulus can be modified to allow for variations in the effect on the muscle tissue.

A specific embodiment of the present invention uses variation of the intensity of the optical stimulus to control activation of motor neurons engineered with light responsive ion channels or pumps. It is believed that different motor neurons will respond differently to light of varying intensities. The differing responses can be particularly useful for selectively producing coarse and fine contractions. Other properties of light that can be used to control responsiveness of motor neurons include, but are not limited to, wavelength, spatial location and temporal properties (e.g., pulse duration or pulse separation).

Motor neurons use electrical signaling to transmit control signals between portions of the nervous system and muscle fibers. The electrical signals take the form of electrical pulses or action potentials. An action potential is a voltage pulse that travels along the membrane of the motor neuron. An action potential is generated when the membrane voltage reaches a threshold voltage level. An action potential of the motor neuron results in the release of chemicals (neurotransmitters). These chemicals cause the muscle fiber to contract.

One embodiment of the present invention uses light to activate light-responsive cation channels in the motor neuron. Light of sufficient intensity and wavelength activates the cation channels, which induces a current in the motor neuron. The induced current moves the membrane voltage toward the threshold voltage necessary to produce an action potential. If sufficient current is induced, an action potential is generated and the muscle fibers of the corresponding motor unit are activated.

One embodiment of the present invention involves introducing light-activated cation channels in one or more motor neurons. One mechanism for introducing the cation channels involves the use of vectors, such as lentiviruses, retroviruses, adenoviruses and phages. The vectors are introduced to the motor neurons and result in expression of the gene for the light-activated cation channels.

Surprisingly and consistent with embodiments of the present invention, it has been discovered that optical stimulation can be used to recruit motor units in a largely normal physiologic order. The number of light-activated channels opened is proportional to the intensity of the light that is applied. Although not bounded by theory, it is believed that the density of light-activated channels (e.g., using vectors) is relatively uniform between different sized motor neurons. As the size of a motor axon increases, the membrane area increases by the power of two, while the motor axon volume increases by the power of three. The number of light-activated channels relates more directly to the membrane area as opposed to the motor axon volume. Therefore, as a motor axon increases in size, the volume increases at a rate such that larger motor axons have fewer light-activated channels per volume. This implies that for a given light intensity, motor neurons of smaller motor units have a faster change in voltage due to the light-activated channels. Accordingly, smaller motor neurons exhibit larger changes in membrane potential than larger motor neurons. Thus with increasing light intensity, the size of motor units recruited also increases, matching the normal physiologic order.

Embodiments of the present invention are implemented with knowledge of these unexpected results. For instance, the optical stimulus profile (e.g., optical intensity, optical frequency or spatial location) can be set as a function of the size of motor unit/neuron to be recruited. A lookup-table or an algorithm can be used to associate a desired muscle response with a particular optical profile. According to one such implementation, the optical stimulus profile can be set according to a muscle fatigue factor. Due to the activation of smaller motor neurons before larger motor neurons, measurements of the muscle fatigue can be used to determine the point at which motor neurons of increasingly larger size are recruited. The experimental results presented herein provide examples of fatigue-based determinations that are consistent with embodiments of the present invention.

Another factor that can be used includes the contractile response (strength and/or speed) of recruited motor units. The contractile response can be correlated to the size of the motor units/neurons that were recruited under a specific optical stimulus profile. The optical stimulus is then determined as a function of the desired contractile response of the muscle. The contractile response can be measured by a variety of different mechanism. Non-limiting examples include force and/or speed measurements caused by muscle contraction or monitoring of muscle activation (e.g., electromyography (EMG) measurements).

Such factors are but a few of the possible mechanisms for determining an optical stimulus profile. Other factors can include, for example, the location, size and/or type of muscle tissue under stimulus. Moreover, different species may require different stimulus profiles and/or different stimulus devices. The age, physical size and fitness of the patient can be used as factors in determining an optical stimulus profile.

Various other determinable factors are contemplated for determining the optical stimulus profile, many of which are facilitated by knowledge of the orderly recruitment of motor units that can be provided by embodiments of the present invention. Accordingly, while the invention is not limited to orderly recruitment of motor units, various embodiments are facilitated by this aspect.

Turning now to the figures, FIG. 1A depicts a peripheral nerve stimulated by optical stimulus devices, consistent with an embodiment of the present invention. Nerve trunk 101 includes nerve bundles 111 and 113. The nerve bundles 111 and 113 are engineered to include light responsive channels/pumps. Optical stimulus devices 103 and 107 provide optical stimulus to the engineered light-responsive channels/pumps. Although not limited thereto, optical stimulus devices 103 and 107 are depicted as light-emitting diodes (LEDs) controlled by optical control circuits 105 and 109, respectively.

In one implementation, a single optical stimulus device 103/107 can be used. In other implementations, multiple optical stimulus devices 103/107 are possible. The optical stimulus devices can operate at the same wavelength of light or at different wavelengths of light. When operating at the same wavelength of light, the use of multiple optical stimulus devices can increase the intensity of the provided optical stimulus, increase the area of optical stimulus and/or provide spatially controllable optical stimulus. For instance, the physical location of the optical stimulus devices can be used as a factor in the stimulation of the light-responsive channels/pumps. Due to relative position of the devices, morphology of the nerve trunk or other factors, the devices can provide different responsiveness of the nerves and associated functions.

Optical control circuits 105 and 109 can also be implemented so that individual control of the optical stimulus devices is possible. This can be particularly useful for implementations where the optical stimulus devices operate at different wavelengths. Different types of light responsive channels/pumps can be designed to have a different wavelength for the optimal responsiveness. In a particular embodiment of the present invention, the differences in the wavelengths are sufficient to allow for activation of one type of light responsive channel/pump without activating the other type of light responsive channel/pump. In this manner, a first type (e.g., ChR2) of channel/pump can be used to facilitate activation (action potentials) in a nerve and a second type (e.g., NpHR) of channel/pump can be used to inhibit activation (action potentials) in a nerve. Other possibilities include the targeting of the first type of channel/pump to a first type of cell (e.g., slow twitch motor unit) and the second type of channel/pump to a second type of cell (e.g., fast twitch motor unit).

These examples show the wide variety of applications and possible applications for embodiments of the present invention. A number of such embodiments, including those discussed in connection with the various figures, are directed to control of muscle fibers through optical stimulation of motor neurons. Other embodiments, some of which are expressly discussed herein, are also contemplated. For instance, peripheral nerves also provide sensory responses (e.g., pain, touch or appetite). A number of disorders are associated with abnormal sensory responses. Accordingly, various embodiments relate to treatment or characterization of various sensory-related disorders.

Figure 1B:
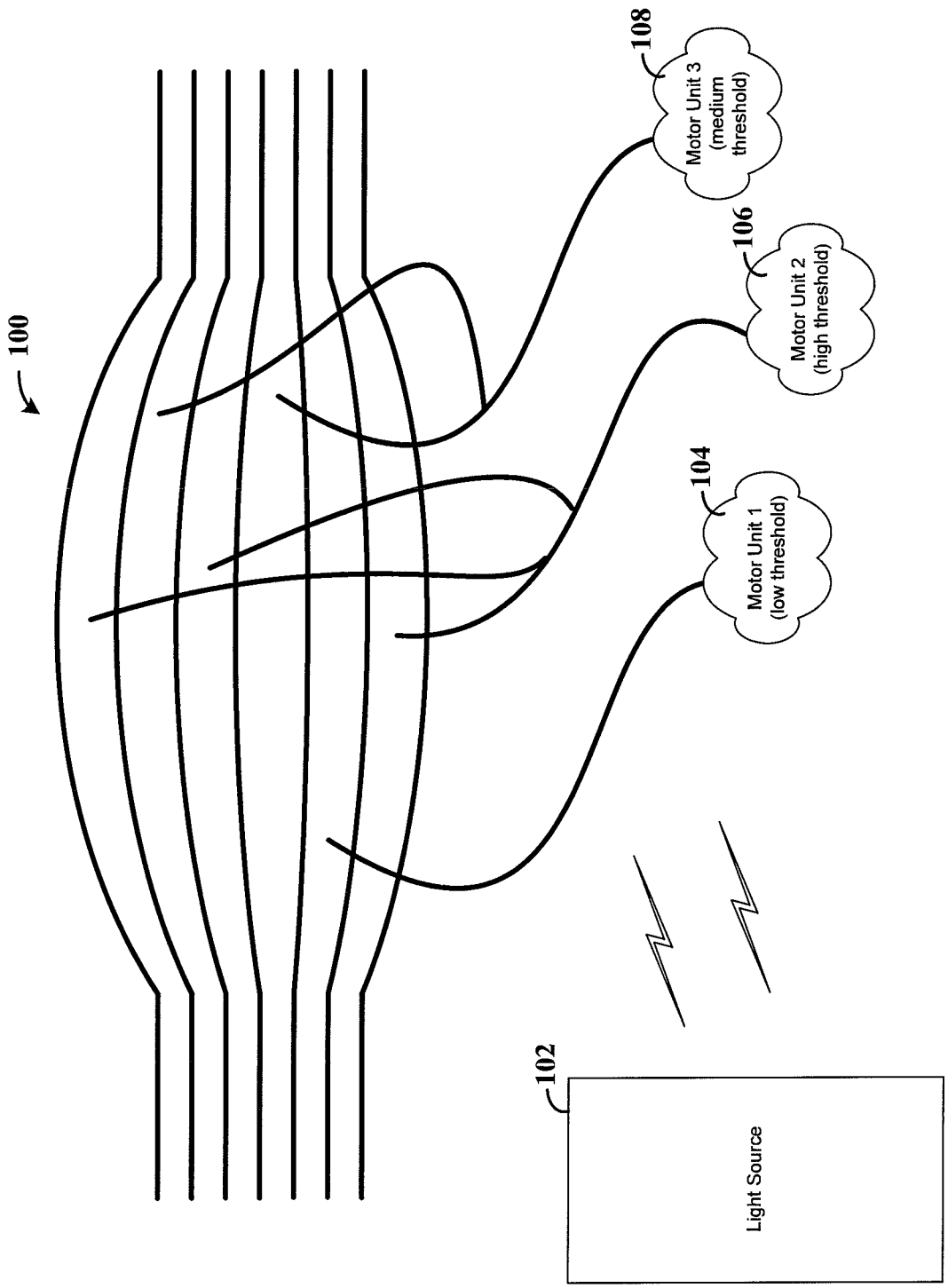
FIG. 1B shows muscle fibers controlled by a set of light-responsive motor neurons, according to an example embodiment of the present invention.

FIG. 1B shows muscle fibers controlled by a set of light-responsive motor neurons, according to an example embodiment of the present invention. Muscle fibers 100 are responsive to motor units 104, 106 and 108. Each motor unit responds to a different motor neuron. Motor unit 104 has a motor neuron with a relatively low threshold, meaning that the motor neuron is responsive to a lower amount of stimulus. Motor unit 106 has a motor neuron with a relatively high threshold, and motor unit 108 has a motor neuron with threshold between the other two motor neurons. Under normal physiologic recruitment, this would allow for the activation of motor unit 104 without activating motor units 106 or 108 and for the activation of motor unit 108 without activation motor unit 106.

In a specific implementation, the motor neurons include proteins/molecules that function as light-activated ion channels or pumps. Light source 102 provides light to the light-activated ion channels or pumps. If the light is sufficient to activate the light-responsive molecules, ion flow across the membrane modifies the membrane voltage of the motor neurons. As the intensity of the light increases, the percentage of light-responsive molecules that are activated also increases. Thus, light intensity can be used to activate the smaller motor units without activation of the larger motor units.

It should be noted that factors other than light intensity can play a role in the activation of the light-responsive molecules. For example, the wavelength of light can also have an effect on activation of motor units. For example, increasing the intensity of light at a specific wavelength may have little or no effect when the wavelength is outside of an effective absorption band (i.e., wavelengths that the molecules respond to) for light-responsive molecules. In another example, shifting the wavelength of the light relative to the effective absorption band can change the percentage of light-responsive molecules that respond without modifying intensity of the light. Other examples involve the duration of the light and/or the spatial location of the delivered light relative to the motor neurons.

In one implementation, the application of the optical stimulus is responsive to a sensed neural activation. For instance, a damaged portion of a nerve can be effectively bypassed by sensing neural activation signals and providing responsive optical stimuli at a point beyond the damaged portion of the nerve. In one implementation, the sensed neural activation can be neural activation within the nerve, but prior to the damaged portion. In another implementation, the sensed neural activation could be from an otherwise unassociated portion of the nervous system. For this second type of implementation, the patient can retrain the neural pathways to control the damaged nerve using the previously unassociated portion of the nervous system. Another example of sensed activation includes sensing muscle activation more directly (e.g., using an EMG). In response to sensed activation, optical stimulus can be provided to recruit additional motor units. In this manner, the muscle activation can be increased by the application of an optical stimulus profile.

Figure 2:
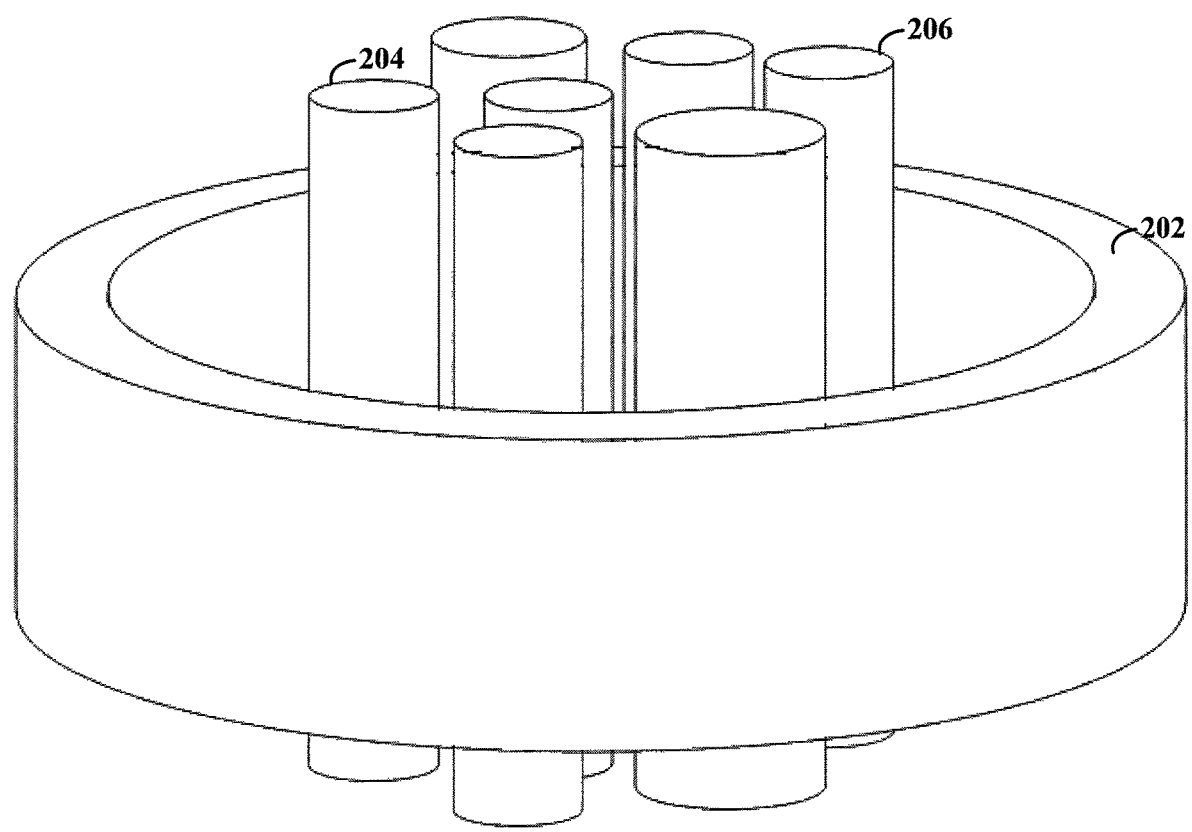
FIG. 2 shows a light stimulation device for placement around peripheral nerves, according to an example embodiment of the present invention.

FIG. 2 shows a light stimulation device for placement around peripheral nerves, according to an example embodiment of the present invention. Light stimulation device 202 surrounds motor neurons 204 and 206. Motor neurons 204 and 206 can be of different sizes, allowing for selective activation thereof. In one implementation, stimulation device 202 can vary the intensity of the generated light as desired so as to allow for selective activation of certain ones of the motor neurons.

Embodiments of the present invention include implementations of light stimulation device 202 that do not surround motor neurons 204 and 206. For example, light stimulation device 202 can be implemented using a U-shaped cuff that is designed to be placed proximate to the motor neurons. Other shapes are possible, including point light sources, such as an optical fiber.

In certain implementations light stimulation device 202 is attached to an arm (not shown) that can be used to guide the light stimulation device 202 near the motor neurons 204 and 206. If desired, the arm can be subsequently removed. Alternatively, the arm can be left in place and used the help fix the position of light stimulation device 202, provide adjustment of the position of light stimulation device 202 and/or provide power/control signals to light stimulation device 202.

Figure 3:
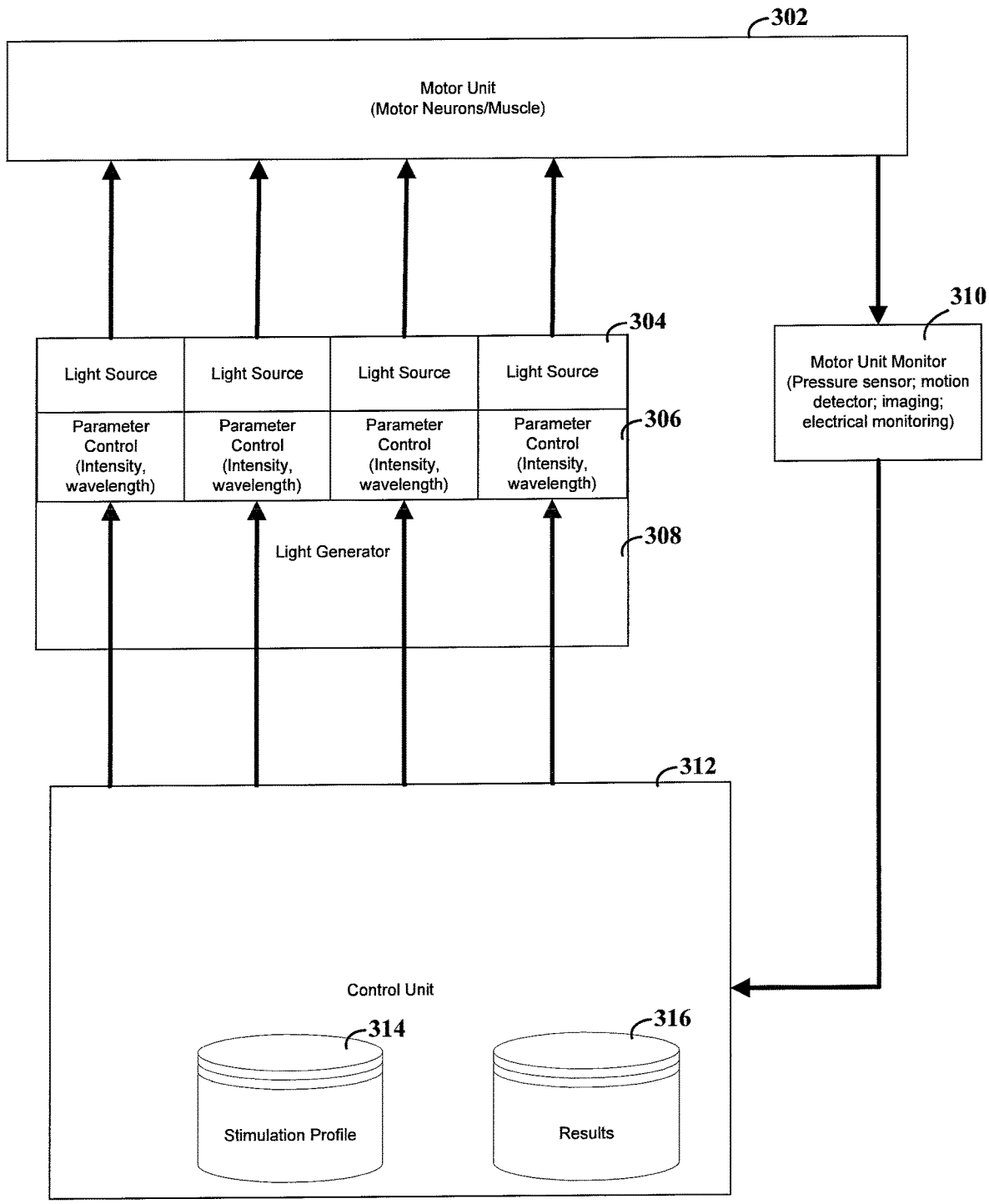
FIG. 3 shows a system for stimulating motor neurons, according to an example embodiment of the present invention.

FIG. 3 shows a system for stimulating motor neurons, according to an example embodiment of the present invention. Motor units (motor neurons and muscle fibers) 302 include light responsive ion channels/pumps. Light generator 308 includes one or more light sources 304 that stimulate the channels/pumps within the motor units. Parameter controls 306 allow for control of light sources 304 by modifying the light properties. The modification of parameters can be implemented so as to allow for activation of some motor units without activating others. For example, the intensity of the light can be set at a level that activates some motor units and not others. In another instance, the wavelength of light can be changed, thereby achieving much the same effect as modifying the intensity of the light. Other possibilities include activating only some of the light sources 304, or using different light parameters for certain light sources 304.

Motor unit monitor 310 provides feedback on the activation of the motor units. The feedback can be implemented using a number of different measurements. For example, motion associated with the muscle can be monitored to determine the strength of the contraction using a pressure sensor, speed of the movement using image capture and/or the preciseness of the movement (e.g., smooth or jerky). In some instances it may also be possible to measure the electrical responsiveness of the motor units. As the stimulus is optical and not electrical, the electrical signals represent the results of the stimulus without separating the (optical) stimulus signals from the (electrical) results thereof. These and other results can be stored in a results database 316.

Control unit 312 can be used to generate stimulus profiles that are used to control the light generator 308. These profiles can be stored within a stimulation profile database 314. In one implementation, a sequence of profiles are implemented and correlated to the results stored in results database 316. The desired muscle response can then be implemented by providing a stimulation profile that is correlated to the desired result.

According to a specific embodiment of the present invention, both inhibitory and excitation molecules are implemented to provide control of the motor units. In certain instances this can provide further delineation between activation of different motor units by, for example, enabling both the inhibitory and excitation molecules. This can effectively reduce the likelihood of a motor neuron action potential (relative to enabling the excitation molecules without enabling the inhibitory molecules). In certain instances, stimulation for inhibition and excitation can be provided at different spatial locations. This can allow for each of the inhibition and excitation stimulus to more strongly affect different motor neurons, respectively.

In one embodiment of the present invention, an implantable device includes a control portion that responds to magnetic fields. This control portion can be implemented as an electrical wire, resistive element or other responsive element. In such an embodiment, the intensity, duration and frequency of light generated would be controlled by the current generated from an introduced magnetic field. This can be particularly useful for creating inexpensive, long lasting and small devices. An example of such an embodiment is discussed further in connection with FIG. 4A and FIG. 4B.

In another embodiment of the present invention, the control portion can be implemented as a more complex circuit. For instance the control circuit may include and otherwise implement different rectifier circuits, batteries, pulse timings, comparator circuits and the like. In a particular example, the control circuit includes an integrated circuit (IC) produced using complementary metal-oxide-semiconductor (CMOS) or other processes. Integrated circuit technology allows for the use of a large number of circuit elements in a very small area, and thus, a relatively complex control circuit can be implemented for some applications.

In a particular embodiment of the present invention, the light generating portion is a blue LED, such as LEDs in 0603 or 0805 package sizes. A particular example is a blue surface mount LED having part number SML0805, available from LEDtronics, Inc (Torrance, Calif.).

Figure 4A:
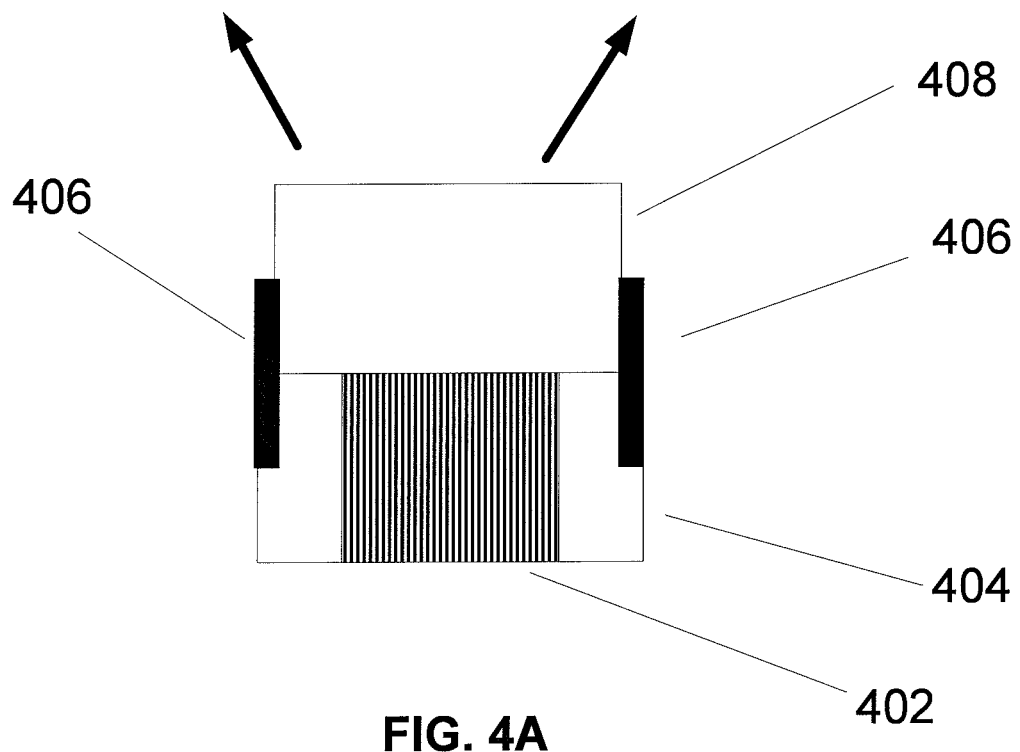
FIG. 4A shows a block diagram of an implantable device, according to an example embodiment of the present invention.
Figure 4B:
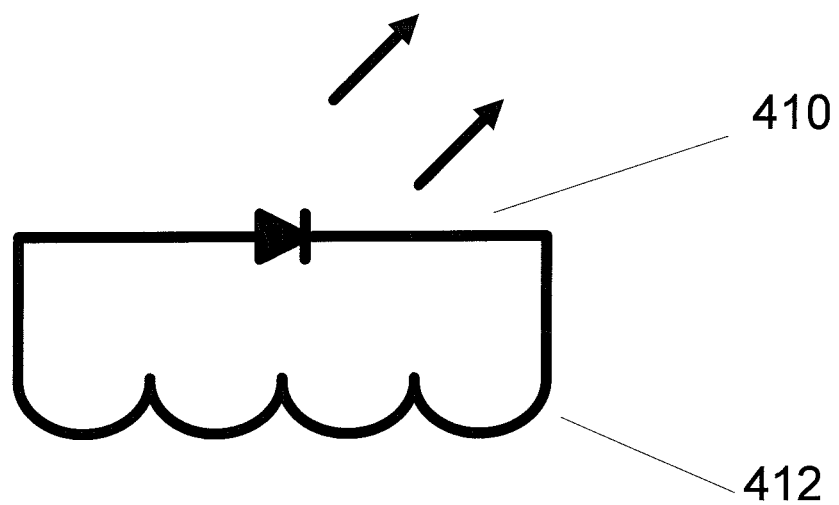
FIG. 4B shows a circuit diagram corresponding to the block diagram of FIG. 4A, according to an example embodiment of the present invention.

FIG. 4A shows a block diagram of an implantable device, according to an example embodiment of the present invention. FIG. 4A shows an inductor comprising coils 402 and core 404 connected to LED 408 using conductive paths shown by 406. FIG. 4B shows a circuit diagram corresponding to the block diagram of FIG. 4A. Inductor 412 is connected in parallel to LED 410. Thus, current and voltage generated by changing a magnetic field seen at inductor 412 causes LED 410 to produce light. The frequency and strength of the changing magnetic field can be varied to produce the desired amount and periodicity of light from LED 410.

Examples of light stimulation devices are taught by International Application No. PCT/US08/50628, entitled System for Optical Stimulation of Target Cells, to Schneider et al., and filed Jan. 9, 2008. The patent document teaches a variety of devices and delivery devices for use with light-responsive molecules. As such, the document is hereby incorporated by reference in its entirety.

There are a number of suitable light-responsive molecules that can be used to modify nerve cells so that the cells are optically responsive. One class of molecules facilitates action potentials in the nerve cells by inducing ionic current that moves the membrane voltage toward the voltage threshold of the cell. In one embodiment of such a molecule, the light-responsive molecule is one of the proteins ChR2, Chop2, ChR2-310, or Chop2-310. In another embodiment, the light-responsive molecule is a 7-transmembrane protein. In another embodiment, the light-responsive molecule is a single-component protein. In yet another embodiment, the light-responsive molecule covalently binds retinal. For further details on light responsive molecules reference can be made to the aforementioned *System for Optical Stimulation of Target Cells*, to The Board of Trustees of the Leland Stanford Junior University, which is fully incorporated herein by reference.

Another class of molecules discourages action potentials in the nerve cells by inducing ionic current that moves the membrane voltage away from the voltage threshold of the cell. In one embodiment, the light responsive molecule is an archaeal light-driven chloride pump (NpHR) from Natronomonas pharaonis. For further details on such light responsive molecules, reference can be made to Zhang et al., (2007) *Multimodal Fast Optical Interrogation of Neural Circuitry*, Nature 2007 Apr. 5; 446(7136):617-9, which is fully incorporated herein by reference. These and other molecules can be used alone or in conjunction with one another.

A few specific examples of light responsive molecules, their use and stimulation devices and techniques (e.g., ChR2 or NpHR) are provided in U.S. patent application Ser. No. 11/459,636, entitled Light-Activated Cation Channel and Uses Thereof, to Boyden et al., and filed Jul. 24, 2006; in International Application No. PCT/US2008/050628, entitled System for Optical Stimulation of Target Cells, to The Board of Trustees of the Leland Stanford Junior University and filed on Jan. 9, 2008; and also in U.S. patent application Ser. No. 12/041,628, entitled Systems, Methods and Compositions for Optical Stimulation of Target Cells, to Zhang et al., and filed on Mar. 3, 2008. These documents teach a number of different light responsive molecules (including, but not limited to, specific sequence listings) as well as variants thereof. These documents include numerous discussions of example molecules as well as delivery and stimulation techniques. As such, these documents are hereby incorporated by reference in their entirety.

A particular embodiment uses a two-part approach: expression of ChR2 (or NpHR in other cases) in the neurons of interest, followed by implantation of a light source to illuminate the nerve at the specified frequency. ChR2 expression can be achieved through "projection targeting", whereby opsin vectors are injected not at the site of eventual illumination, but at a distant site where the cell bodies of the target neurons lie. Alternately, target muscles can be infused with a retrograde virus; in this approach, one does not need to know cell type-specific promoters, and only the axons of the targeted cells are optically modulated even though they may be intermixed with other cell types in the nerve. Unlike other optically-responsive channels that have been developed, although ChR2 and NpHR require an all-trans-retinal (ATR) chromophore as a cofactor, retinoids naturally present in mammalian cells are sufficient.

A specific implementation uses an LED-based nerve cuff, where several micro LEDs are embedded in a solid, optically transparent cuff, and surgically placed around the desired nerve. This cuff provides high intensity light source for stimulating the desired nerve. A specific example light intensity for ChR2 stimulation is >1.0 mW/mm$^2$ light power density. Embodiments of the present invention allow for alternatives to LEDs, such as solid state laser diodes, or some future technology. Considerations for selection of the light source can include efficiency concerns in terms of size, expense, heating, and battery life.

The following description provides details relating to an experimental mouse model for such therapies, as well as evidence that optical stimulation recruits muscle fibers in a normal (healthy) physiologic order, thereby avoiding the problem faced by electrical stimulation. Human nerves are generally larger and the technology is therefore scaled accordingly, however, the same principles of operation can be used.

Muscle parameters were measured in vivo to characterize motor unit recruitment. Motor unit recruitment is often characterized by stimulating individual motor axons from the peripheral nerve at the ventral root. In small animals such as mice, however, this technique is impractical.

FIG. 5A shows a stimulation cuff (e.g., synthesized optical light source) for placement around a peripheral nerve, consistent with an embodiment of the present invention. The stimulation cuff 502 is depicted as having a curved portion designed to at least partially surround the peripheral nerve, however, other embodiments allow for variations including, but not limited to, a cuff that predominantly surrounds a peripheral nerve and point light sources. In the experiment, both electrical and optical stimuli were provided to an anesthetized Thy1-ChR2 mouse by way of such a cuff. The experiment was carried out using an optical cuff (and compared to an electrical cuff) around the sciatic nerve of an adult Thy1-ChR2 or control (C57bl/6) mouse. Stimuli were provided by the cuff to evoke an electrical and contractile response of the muscle.

FIG. 5B shows the muscles electrical response (M-wave) as measured by fine wire electrodes placed in the muscle belly and near the Achilles tendon, consistent with an embodiment of the present invention. The waveform depicts an electromyography (EMG) plot of typical twitch from optical stimulation.

FIG. 5C shows the contractile force output as measured by a force transducer attached to the Achilles tendon, consistent with an embodiment of the present invention. In a mouse, the medial gastrocnemius (MG), the lateral gastrocnemius (LG) and the soleus (SOL) have free tendons that attach to the distal end of the Achilles tendon. To measure muscle forces of an individual muscle, the free tendons of the muscles not being measured are detached. The detached Achilles tendon was fixed to a force transducer to measure muscle contractions. The force traces show typical titanic contractions at various frequencies using optical stimulation.

FIG. 5D depicts EMG and force traces from twitches elicited by optical and electrical stimulations in both Thy1-ChR2 animals and control C57bl/6 animals, consistent with an embodiment of the present invention. These traces show that typical twitch response generated by optical stimulation from the MG does not have a significantly different shape than twitches evoked by electrical stimulation in either Thy1-ChR2 or control animals. The exception to this observation is the absence of a stimulation artifact in the EMG response just prior to the initiation of depolarization under optical stimulation, but seen in all cases of electrical stimulation. There was no response to optical stimulation in control animals, which implies that optical stimulation occurs by photostimulation of the ChR2 channels and not by heat or other electrical means.

Figure 6A:
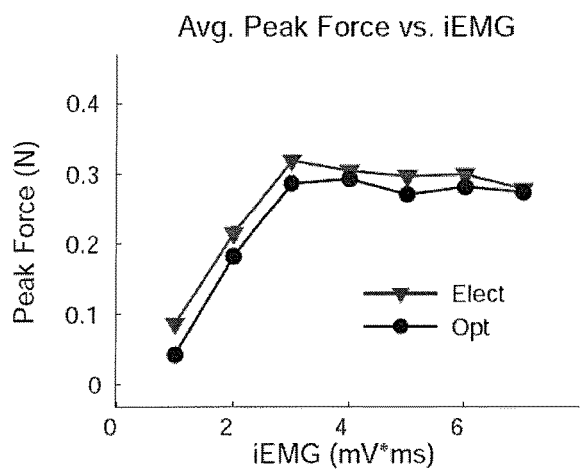
FIG. 6A shows peak force during a single twitch vs. rectified integrated EMG for both electrical and optical stimulations, consistent with an embodiment of the present invention.

To compare electrical and optical stimulation intensities the rectified integrated EMG (iEMG) was used over the time of non-zero activity in each trial. To verify that measurement of iEMG represents a common response of the muscle under both electrical and optical stimulation and also to verify that optical stimulation can elicit contractile forces comparable to electrical stimulation, the average peak force during a twitch was compared to the iEMG response. FIG. 6A shows peak force during a single twitch vs. rectified integrated EMG for both electrical and optical stimulations, consistent with an embodiment of the present invention. For a given iEMG, both optical and electrical stimulations produce similar trends, but the peak twitch forces were on average 15.4% lower using optical stimulation. Average peak twitch forces using electrical stimulation (0.32±0.05 N) were significantly higher ($p<0.01$) than average twitch forces with optical stimulation (0.29±0.01 N), possibly indicating that most but not all motor neurons are stimulated under optical stimulation. Twitch forces produced by electrical and optical stimulation are consistent with previous measurements.

Figure 6B:
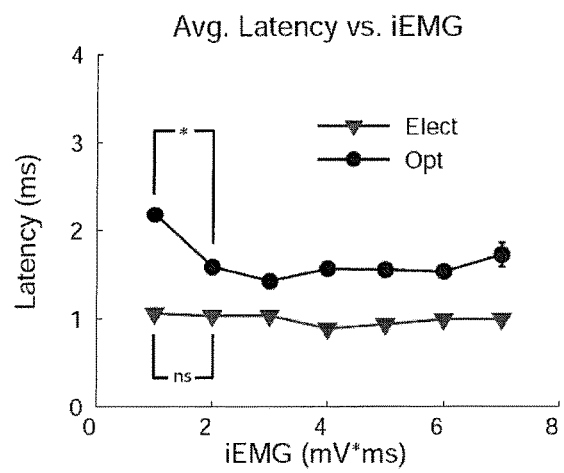
FIG. 6B depicts average latency measured from initiation of stimuli to detection of EMG, consistent with an embodiment of the present invention.

Measurement of motor axon conduction latency is the most common method used to estimate motor unit recruitment. Smaller axons have slower conduction speeds, and therefore have longer latencies for a given distance. FIG. 6B depicts average latency measured from initiation of stimuli to detection of EMG, consistent with an embodiment of the present invention. Latency represents the time difference between the initiation of the stimuli and the depolarization measured on EMG (M-wave). Latencies measured under optical stimulation for all intensities (2.18±0.02-1.72±0.13 ms) were significantly longer than those under electrical stimulation (1.15±0.05-0.99±0.01 ms, $p<0.01$ in all cases). This difference is possibly due to lower cation conductance of ChR2 channels, which delays the formation of an action potential. The conduction velocity was estimated (32.2-40.4 m s−1), due to significant uncertainty in the path length of the axon from the site of stimulation to site of measurement and found to be consistent with expected values. At the lowest levels of activity, the drop in latency from 1 mV ms to 2 mV ms under optical stimulation was significant ($p<0.01$) while the difference under electrical stimulation was not ($p=0.11$). This implies that smaller axons are recruited preferentially at the lowest levels of optical stimulation but not under electrical stimulation.

Figure 6C:
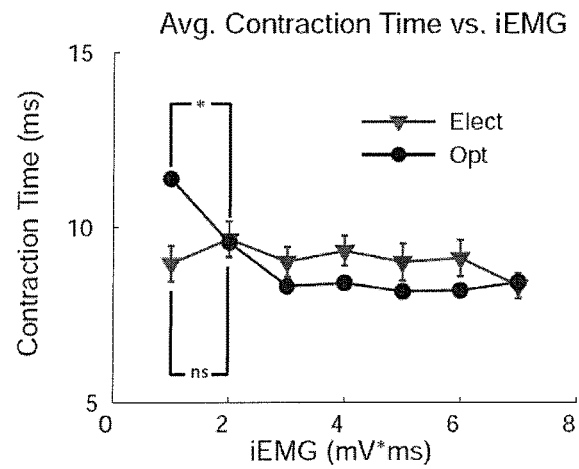
FIG. 6C shows the average contraction time measured from 10% of peak force to peak force, consistent with an embodiment of the present invention.

Other measures of motor unit recruitment, such as the contraction and relaxation times, were found to suggest orderly recruitment with optical stimulation. FIG. 6C shows the average contraction time measured from 10% of peak force to peak force, consistent with an embodiment of the present invention. Under optical stimulation (11.1±0.08 ms), the contraction time was significantly longer at the lowest levels of muscle activity than electrical stimulation (8.79±1.01 ms, p<0.01). While at the highest levels of muscle activity, contraction time under optical and electrical stimulation was not found to be significantly different (8.34±0.07 ms, p=0.60).

Figure 6D:
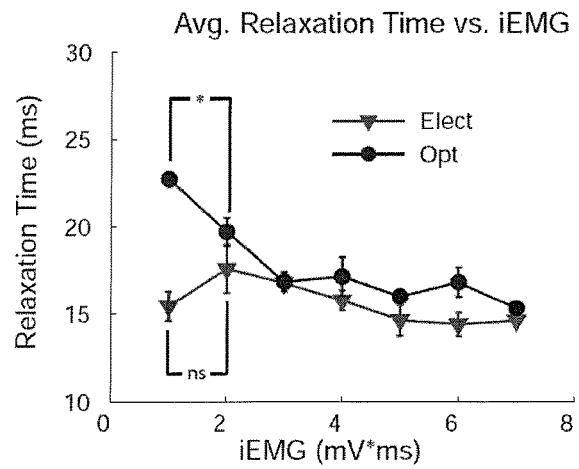
FIG. 6D depicts average relaxation time measured from peak force to 10% of peak force, consistent with an embodiment of the present invention.

FIG. 6D depicts average relaxation time measured from peak force to 10% of peak force, consistent with an embodiment of the present invention. This relaxation time was significantly longer at the lowest level of muscle activity with optical stimulation (21.73±0.39 ms) than electrical stimulation (17.46±0.68 ms, p<0.01), whereas relaxation time at the highest levels of muscle activity were not significantly different between the different types of stimulation (14.540.09 ms, p=0.10). The measurements of contraction and relaxation time, which are consistent with earlier in vitro data, both imply that at the lowest levels of muscle activity, optical stimulation preferentially recruits slower motor units than electrical stimulation.

To further examine differential motor unit recruitment, the recruitment of two different muscles, soleus (SOL) and lateral gastrocnemius (LG), were compared. FIG. 7A shows rectified-integrated EMG (iEMG) vs. estimated optical intensity at surface of the sciatic nerve for soleus (SOL) and lateral gastrocnemius (LG), consistent with an embodiment of the present invention. Whereas FIG. 7B shows rectified-integrated EMG vs. electrical stimulation voltage applied to the sciatic nerve, consistent with an embodiment of the present invention.

SOL contains 58±2% slow oxidative (SO) fibers and 0% fast glycolytic (FG) fibers, while LG has 69±13% FG fibers and 1±3% SO fibers. It has been reported that smaller motor units tend to have higher compositions of SO fibers, and therefore, it was expected that SOL motor units would be recruited prior to the faster motor units of LG, an observation that has been reported in physiological recruitment studies. FIG. 7C shows optical intensity required to achieve maximum iEMG in SOL and LG, consistent with an embodiment of the present invention. Under optical stimulation SOL (14.9±1.9 mW mm-2) reaches 95% peak activity at a significantly lower optical intensity than LG (FIG. 7C, 24.4±1.9 mW mm-2, p<0.01). At the lower levels of optical stimulation, LG and SOL have similar levels of activity. This observation can be attributed to the possibility that LG contains small motor units composed of fast muscle fibers.

FIG. 7D shows electrical stimulation required to achieve 95% of maximum iEMG in SOL and LG, consistent with an embodiment of the present invention. The electrical stimulation used to evoke 95% of peak activity in SOL (0.64±0.15 V) and LG (0.64±0.09V) was not significantly different (FIG. 7D, p<0.01). These findings suggest that slower muscle fibers are preferentially recruited by optical stimulation before faster fibers; however, the order of motor unit recruitment would be more certain given knowledge of the size distribution of the motor axons innervating each muscle.

To analyze axon size distribution, and to determine if there was bias in the location of the axons innervating each muscle within the cross-section of the peripheral nerve, retrograde dye (Fast Blue) was intramuscularly injected into the muscles of interest to backfill only the axons innervating the muscle in which it was injected. FIG. 7E shows an example cross-section of the sciatic nerve where retrograde dye was injected into the LG only, scale bar=100 g, consistent with an embodiment of the present invention.

FIG. 7F shows distribution of motor axon diameters for SOL and LG found in cross-section of the sciatic nerve, consistent with an embodiment of the present invention. FIG. 7G shows depth of motor axons for SOL and LG found in cross-section of the sciatic nerve, consistent with an embodiment of the present invention.

In cross-sections of the sciatic nerve (FIG. 7E) SOL and LG do not contain significantly different numbers of motor axons (FIG. 7F, 53.5±4.9, 55±3.7, p=0.71). However, the average motor axon innervating LG had a significantly larger Feret's diameter than those innervating SOL (6.7±0.16 μm, 4.5±0.17 μm, p<0.01). No bias was observed as to the location of either set of axons within the peripheral nerve so that one set would be exposed to significantly higher light intensities than another. These observations support the premise that small motor units are preferentially recruited under optical stimulation, and that the observed difference in optical intensity required for peak muscle activity in SOL and LG is not influenced by either number of axons or position of those axons in the peripheral nerve.

Figure 8A:
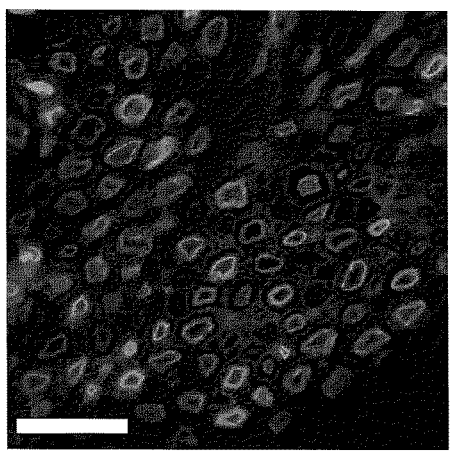
FIG. 8A depicts a confocal image of sciatic nerve in cross-section, consistent with an embodiment of the present invention.
Figure 8B:
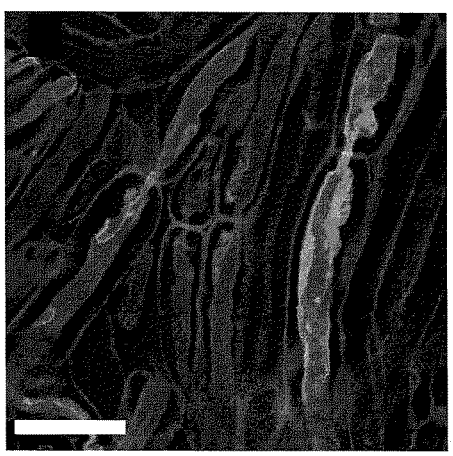
FIG. 8B depicts a confocal image of sciatic nerve in a longitudinal section with the same staining as in FIG. 8A, illustrating several nodes of Ranvier (gaps formed between myelin sheaths of cells), scale bar is 50 μm, consistent with an embodiment of the present invention.

To determine the location of the ChR2 channels within the motor axons and whether there were any differences in expression levels in relation to the size of the motor axons, cross-sections of the sciatic nerve were made both parallel and perpendicular to the long axis of the motor axons. FIG. 8A depicts a confocal image of sciatic nerve in cross-section, consistent with an embodiment of the present invention. The first channel is due to anti-laminin labeling basal lamina of the peripheral nerve. The second channel is due to YFP fluorescence expressed natively in the transgenic neurons, scale bar is 50 μm. FIG. 8B depicts a confocal image of sciatic nerve in a longitudinal section with the same staining as in FIG. 8A, illustrating several nodes of Ranvier, scale bar is 50 μm. The ChR2 channels are labeled with yellow fluorescent protein (YFP), so the average relative YFP fluorescence intensity of axons was compared to the diameter of those axons using confocal microscopy.

Figure 8C:
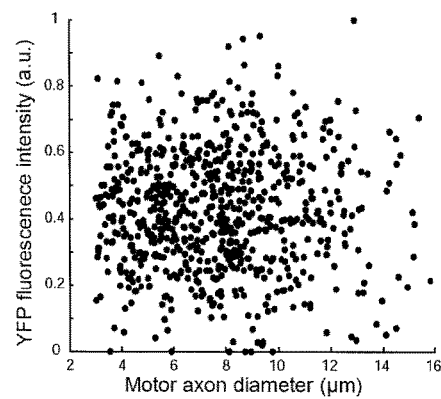
FIG. 8C shows YFP fluorescence intensity versus motor axon size in cross-section (n=4), consistent with an embodiment of the present invention.

FIG. 8C shows YFP fluorescence intensity versus motor axon size in cross-section (n=4), consistent with an embodiment of the present invention. No correlation was found between axon size and fluorescent intensity in the transverse sections (FIG. 8C, $R^2$=0.0021, p=0.88). Additionally it was possible to locate nodes of Ranvier within the cross-sections (FIG. 8B).

Figure 8D:
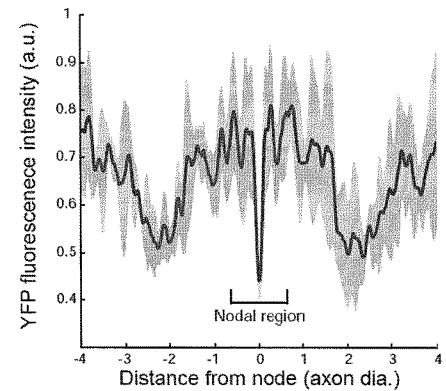
FIG. 8D shows the average fluorescence intensity parallel to the long axis of sampled axons, where the origin indicates the center of the node of Ranvier (n=15, shaded region is standard deviation (s.d.)), consistent with an embodiment of the present invention.

FIG. 8D shows the average fluorescence intensity parallel to the long axis of sampled axons, where the origin indicates the center of the node of Ranvier (n=15, shaded region is s.d.), consistent with an embodiment of the present invention. The fluorescence, and presumably the ChR2 channel density, varies along the axolemma. Fluorescence intensity at center of the nodal region is at a minimum, while fluorescence intensity in the peri-nodal region is at a maximum. It is known from immuno-localization studies that the center of the nodal region contains high concentrations of $Na^+$ channels, which is likely the cause of the lower fluorescent signal is this region. Additionally, the nodal and internodal regional morphology appears normal, giving no indication for abnormal behavior of the transgenic motor neurons.

Figure 9A:
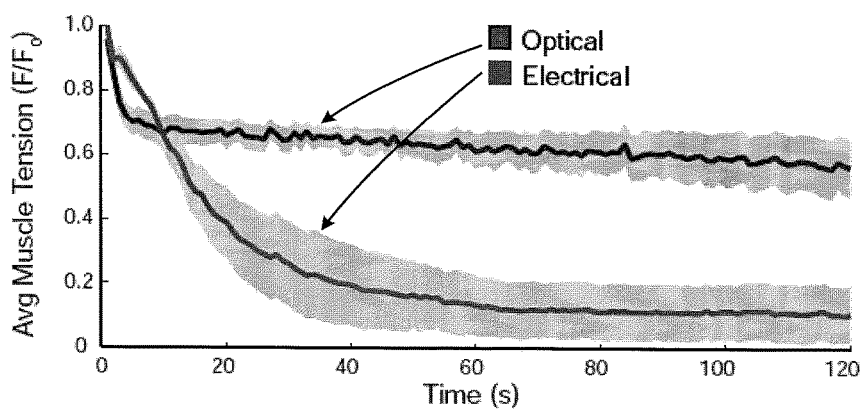
FIG. 9A shows the average tetanic tension over two minutes in muscle being stimulated with 250 ms trains at 1 Hz using electrical and optical stimulation (n=7, shaded region is standard error (s.e.)), consistent with an embodiment of the present invention.
Figure 9B:
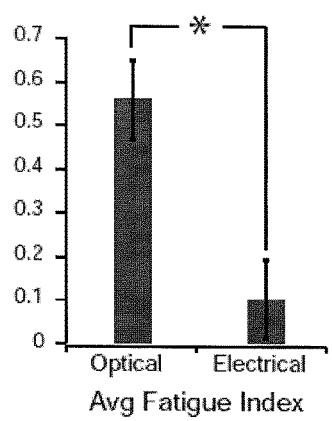
FIG. 9B shows the average fatigue index for electrical and optical stimulation, measured as decline in tetanic tension over two minutes (n=7, error bars are s.e., * indicates p<0.01), consistent with an embodiment of the present invention.
Figure 9C:
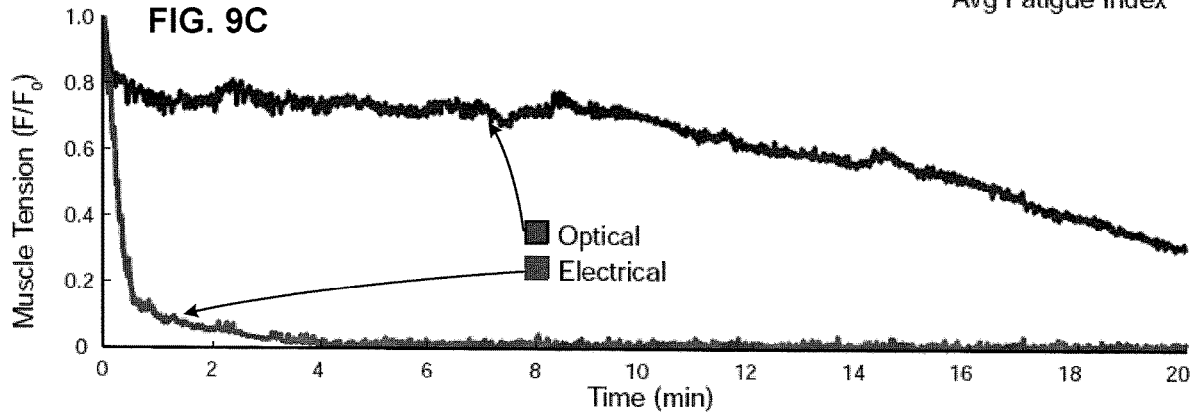
FIG. 9C shows an example of tetanic tension taken from a single mouse using both optical and electrical stimulation in contralateral hindlimbs over 20 minutes, consistent with an embodiment of the present invention.

The ability to preferentially recruit slower motor units with optical stimulation has potentially enormous functional significance. Functional Electrical Stimulation (FES) systems have been developed to serve as neuro-prosthetics for patients with paralysis, but have not been adopted widely because of early onset fatigue possibly due to reverse recruitment by electrical stimulation. To test whether optical stimulation of muscle elicits less fatigue than electrical stimulation, measurements were taken of tetanic tension generated by the plantar flexor group of Thy1-ChR2 mice using both stimulation types. FIG. 9A shows the average tetanic tension over two minutes in muscle being stimulated with 250 ms trains at 1 Hz using electrical and optical stimulation (n=7, shaded region is s.e.), consistent with an embodiment of the present invention. FIG. 9B shows the average fatigue index for electrical and optical stimulation, measured as decline in tetanic tension over two minutes (n=7, error bars are s.e., * indicates p<0.01), consistent with an embodiment of the present invention. Using stimulation intensities in each modality that elicited 2X body weight for each unfatigued mouse, 1 Hz stimulation trains were used for 2 minutes, with each train lasting 250 ms. The average fatigue index, measured as the average tetanic tension of the last train divided by the average tetanic tension in the first train, declined significantly lower in trials using electrical stimulation (0.11±0.09), than those using optical stimulation (0.56±0.09, p<0.01). Additionally, when this fatigue protocol is extended to 20 minutes in an individual mouse using contralateral hindlimbs, electrical stimulation diminishes tetanic tension to ~0% after just 4 minutes, while optical stimulation continues to elicit 31.6% of its initial tension after the entire 20 minute trial. FIG. 9C shows an example of tetanic tension taken from a single mouse using both optical and electrical stimulation in contralateral hindlimbs over 20 minutes, consistent with an embodiment of the present invention.

Physiological measurements were taken according to the following methodology. Normal appearing, 9-12 week old Thy1-ChR2 or C57bl/6 control mice were anesthetized and the hindlimb was shaved and fixed in a frame. The Achilles tendon was freed by cuffing the distal end of the calcaneous to a force transducer (Aurora Scientific, 300CLR) by thin steel wire. An optical cuff, made of 16 LEDs (Rohm, SMLP12BC7T, 465 nm) arranged in a concentric perimeter facing the peripheral nerve center, or a bipolar hook electrical cuff was inserted around the exposed sciatic nerve that is cut proximal to the site of stimulation. In most cases optical and electrical stimulation were conducted in the same leg at different times. Stainless steel hook electrodes were inserted for differential EMG recordings. EMG recordings were filtered in hardware only (BP 3-3000 Hz). All force, EMG, and stimuli data were sampled at 100 kHz.

Imaging was implemented consistent with the following steps. Fresh sciatic nerve was fixed in 4% PFA for 30 min and washed in PBS. The samples were then embedded in 5% low-melting point agarose and cut (50 µm) with a vibratome. The sections were labeled with anti-tau and anti-lamin. The sections are imaged on a confocal microscope (Leica, DM6000). The number, size and fluorescence intensity of the motor axons (≥3 µm and G-ratio≥0.5)33, 34 were determined by manual analysis in ImageJ.

All other data analysis was conducted in Matlab. All data reported for the MG was broken in arbitrarily defined bins based on iEMG value. To determine stimuli needed for 95% maximum iEMG in SOL and LG, a Weibull cumulative distribution function was fit to data points. The confidence interval (c.i.) generated by the curve fit was used to define the 99% c.i. of the required stimuli.

Samples tested for statistically significant differences were first tested for normality using Lilliefors test ($\alpha=0.05$), then tested using unpaired two-tailed Student's t-test ($\alpha=0.05$). All sample groups tested were found to be of normal distribution, except for the axon size data which was tested using the Mann-Whitney U-test. All data points listed are mean±s.e.m. or data±99% confidence interval (c.i.) when referring to FIGS. 7C and 7D.

The specific implementations of the above-mentioned experiment, while instructive, are not meant to be limiting. The results, however, show the versatility and broad-applicability of related methods, devices and treatments, some of which are discussed hereafter.

In a specific implementation, the desired physiologic order is exaggerated by expressing inhibitory NpHR in the fast-twitch fiber motor neurons, providing a method to reduce or prevent fatigable muscle usage when not desired. This, however, might require long periods of yellow light production, causing possible heating and reduction of battery life. Mutant forms of channel rhodopsin that respond to different light frequencies can be used by expressing these different forms of ChR2 in slow and fast twitch fiber motor neurons, thereby creating a definitive system where each could be controlled separately using the different light frequencies. Variations and combinations are contemplated including, but not limited to, multiple forms of ChR2 used in combination with NpHR.

Targeted expression can be accomplished using a cell specific promoter. Examples of cell specific promoters are promoters for somatostatin, parvalbumin, GABA$\alpha$6, L7, and calbindin. Other cell specific promoters are promoters for kinases such as PKC, PKA, and CaMKII; promoters for other ligand receptors such as NMDAR1, NMDAR2B, GluR2; promoters for ion channels including calcium channels, potassium channels, chloride channels, and sodium channels; and promoters for other markers that label classical mature and dividing cell types, such as calretinin, nestin, and beta3-tubulin.

Other aspects of the present invention use spatial properties of the light stimulus to control the activation of the desired motor neurons. For instance, the use of a LED-based nerve cuff, e.g., a stimulation device 202, includes controllable light sources that provide illumination from respective portions of the cuff. The light sources in the different portions of the illumination device are designed to be separately addressable. Calibration techniques can be used to determine the optimal stimulus profile. For example, it may be determined that optical stimulation from a first portion of the illumination device activates higher percentage of fast twitch fiber motor neurons with respect to optical stimulation from another portion of the illumination device. Optical stimulus from this portion can be reduced or avoided altogether when fine motor control is desired. Similarly, when NpHR is used, yellow light can be used from such a portion to reduce activation of fast twitch motor neurons.

According to embodiments of the present invention, an optical stimulation system is configured to provide graduated levels of optical stimulation according to the desired muscle contraction strength. For fine motor control, the optical stimulation is relatively low and/or targeted at the slow twitch motor neurons. For increasingly strong and/or rapid contractions, additional motor neurons are recruited including the fast twitch motor neurons. The graduated levels can be implemented as a function of the respective ratio of fast to slow twitch motor neurons that are responsive to a particular aspect of the optical stimulation. Example aspects include the optical wavelength, optical intensity, duration of optical stimulus and/or the location of the optical stimulus. A stimulation profile can then be determined to provide the desired responsiveness ranging from slow/fine control to fast/coarse control of the particular muscle group. This can be implemented using an algorithm that takes a desired response and determines the optical parameters corresponding to the response. Alternatively, a look-up table, having stored optical parameters that are indexed according to the desired motor response, can be used.

Optogenetic techniques offer novel therapies in several areas. Example applications include, but are not limited to, muscle stimulation, spasticity, tremor, chorea suppression, pain management, vagus, phrenic, and sacral nerve stimulation, cardiac arrhythmia management, and stem cell therapies.

Embodiments of the present invention relate to treatment or characterization of a patient suffering from spasticity. Spasticity is a devastating and common human clinical condition that arises as a result of neonatal injury (e.g., cerebral palsy), genetic disease (e.g., Niemann-Pick disease) and postnatal injury (e.g., spinal cord injury and stroke), and is characterized by hyperreflexia which leads to involuntary muscle contraction in response to movement. Spasticity limits the daily activities of more than millions worldwide, and is estimated to cost billions of dollars in the United States alone. There are a number of medical and surgical treatments for spasticity, including botulinum toxin, intrathecal baclofen, selective dorsal rhizotomy, and gene therapy; however most, if not all, can cause significant side-effects, have limited efficacy, and can be prohibitively expensive. It is extremely difficult to "turn down" the overactive nerves that cause severe muscle contraction, abnormal posture, and pain, since drug approaches are slow and nonspecific with regard to cell type, and electrodes cannot effectively or precisely turn down neural activity, or attain cell type specificity. In many cases physicians will resort to risky surgeries like dorsal rhizotomy, but this can only be done in a minority of spastic patients and has inconsistent efficacy with the potential for serious adverse events.

Consistent with an embodiment of the present invention, both ChR2 and NpHR channels/pumps are expressed in the affected motor neurons, and a nerve cuff, or other light source capable of producing both yellow and blue light, is placed around the nerve. The combination of both ChR2 and NpHR allows for spasticity to be reduced while maintaining muscle function and strength. The stimulation pattern could either be based on a learned feedback pattern (such as those used to control prosthetic limbs) or could be controlled more explicitly by the user (deciding, for example, to leave the muscle limp for a period of time in order to rest).

For instance, the spastic motor control can be effectively overridden using a combination of ChR2 and NpHR stimulation. Electromyography devices can be used to detect the activation signal of muscles, e.g., a sensor/microchip can be implanted in muscles to detect electrical signals from the brain. These signals are transformed into corresponding optical stimulus. A trained technician or biomedical engineer can configure an initial (coarse) response relative to the optical stimulus device. Over time the patient can learn to finely control the optical stimulus device so as to perform the desired movements.

In a similar manner, optogenetic therapy is used to control tremors or various forms of chorea. Motion detection coupled in a feedback manner to ChR2 and NpHR stimulation could effectively provide a low-pass filter for muscle activation, or one in which certain patterns of activation (the specific tremor or choreic motions) were dampened. For example, accelerometers or gyros can be used to provide motion-detection associated with the muscle responsive to the stimulation. In response to motion exceeding a threshold level of forcefulness, speed and/or repeated motions, dampening stimulation can be provided. The threshold level can be adjusted to allow for suitable movement by the patient while also providing sufficient dampening functionality. The optical stimulation device can have an adjustable setting for this dampening functionality.

In one implementation, one or more additional accelerometers or gyros can be placed at the core of the patient. These accelerometers or gyros detect motions associated with the entire individual rather than a specific limb or other body part. When such motion is detected, it can be used to distinguish between motions caused by external forces (e.g., riding in a vehicle) from unwanted spastic motions.

Other embodiments of the present invention relate to treatment or characterization of chronic pain. Millions of people are adversely affected by chronic pain. Chronic pain causes billions of dollars a year in medical costs, lost working days, and workers compensation, and is a major risk factor for depression and suicide.

Pain can be divided into two general categories: nociceptive and neuropathic. In the former, mechanical, thermal, or chemical damage to tissue causes nociceptor response and initiates action potentials in nerve fibers. Afferent fibers terminate directly or indirectly on transmission cells in the spinal cord that convey information to the brainstem and midbrain. Neuropathic pain, in contrast, involves a miscoding of afferent input; mild inputs yield dramatic pain responses, through mechanisms that are not well understood. Often this is the result of an initial nociceptive pain that, instead of resolving with healing of the initial stimulus, proceeds to spontaneous pain and low-threshold for light touch to evoke pain. It is believed that increased sodium channel and decreased potassium channel expression in dorsal root ganglia, the development of "cross-talk" between adjacent afferents, or an increase of glutamate release in spinal cord neurons are among the possible mechanisms for this increased pain sensitivity.

Treatment of pain depends on many factors, including type, cause, and location. There are myriad options, most notably topical agents, acetaminophen and NSAIDs, anti-depressants, anticonvulsant drugs, sodium and calcium channel antagonists, opioids, epidural and intrathecal analgesia, acupuncture and other alternative techniques, botulinum toxin injections, neurolysis, cryoneurolysis, spinal cord stimulation, neurosurgical techniques, radiofrequency ablation, peripheral nerve stimulation, transcutaneous electrical nerve stimulation, and rehabilitation therapy.

So many treatments exist, however, because each has limitations. For example, local anesthetic drugs block sodium channels, preventing neurons from achieving action potentials. However, effectiveness of this treatment is limited by the degree to which specificity for pain neurons can be maintained, avoiding the side effects of numbness or paralysis from blocking other sensory or motor fibers (as well as potential cardiac effects should the drug travel further through the circulatory system). In order to achieve this, low dosages are needed, requiring frequent administration of the drug. Additionally, not all kinds of pain react to local anesthetic treatment, and some cases become refractory over time, or require ever increasing doses.

Surgical treatments, including dorsal or cranial nerve rhizotomy, ganglionectomy, sympathectomy, or thalomatomy, are more drastic options, appropriate in certain severe cases. However, relief from these is unpredictable;

notably, it is sometimes only temporary, and may involve complications. Spinal cord stimulation (SCS) is also used in some cases, attempting to limit chronic pain through placement of electrodes in the epidural space adjacent to a targeted spinal cord area thought to be causing pain; however, a recent review found limited evidence of the effectiveness of this technique.

Alternately, pain can be addressed in the brain. As it is correlated with depression and anxiety, pain is sometimes responsive to antidepressant and anti-anxiety medications such as the tricyclics. Recent promising research suggests the effect of real-time fMRI biofeedback, where patients learn to decrease activation of the rostral anterior cingulate cortex, with resultant reduction in perceived pain. While each of these methods is effective in some cases, chronic pain remains a largely intractable problem. NpHR and ChR2 expression in peripheral afferent nerves is therefore used to influence pain signals.

Control of the peripheral afferent fibers with the high temporal precision of optogenetic techniques offers the ability to inhibit pain signals at a given moment, as with local anesthetic treatment. For instance, NpHR can be engineered in afferent nerves and optical stimulus can be provided to the NpHR to provide anesthetic treatment. The optical stimulus can be relatively constant or responsive to an external control. For instance, a doctor or patient can control the delivery of the optical stimulus in terms of frequency of stimulus, intensity of stimulus or simply turn the stimulus on or off. The temporal properties of ChR2 and NpHR can also be used to interface with and reprogram pain recognition in the CNS. Reprogramming can be implemented as suggested by electrical stimulation, antidepressant medication and biofeedback mechanisms.

The temporal precision and nerve specificity of optogenetic stimulation is particularly useful for reprogramming pain recognition circuits. Response to pain can be "turned up" in neuropathic conditions, creating hypersensitivity to afferent stimulation, suggesting that it is possible to reverse this through other patterns of stimulation. Particular embodiments relate to stimulating pain fibers and larger sensory fibers separately, as larger sensory fiber messages tend to overwhelm and turn down pain fiber recognition.

Embodiments of the present invention also relate to vagus nerve stimulation. The vagus nerve is composed of both afferent and efferent pathways. In the peripheral nervous system, vagal afferent fibers innervate the heart, vocal cords, and other laryngeal and pharyngeal muscles, and also provide parasympathetic input to the gastrointestinal viscera. Afferent fibers project mainly to the brain, in such regions as the pontine and midbrain nuclei, the cerebellum, thalamus, and cortex.

Given this variety of nerve function, vagus nerve stimulation is used for a wide range of treatments, including appetite management, cardiac rate suppression, depression, and epilepsy. In the latter two, effectiveness of the treatment is not well understood. The right vagus nerve provides more innervation to the cardiac atria than the left vagus nerve does, so in situations where cardiac effects are not desirable, electrical stimulation is generally performed on the left side. However, even with these precautions, side effects such as hoarseness, throat pain, coughing, shortness of breath, tingling, and muscle pain are relatively common in patients receiving vagus nerve stimulation. Even more dangerous, bradycardia followed by transient asystole is reported in association with tests during stimulator implantation and there is one case report of bradycardia and asystole with syncope in a patient after two years of wearing the device.

Optogenetic techniques are particularly useful for parsing through the various functions of the vagus nerve and to stimulating only the particular neurons that are of interest. Selective stimulation mitigates the unwanted side effects, particularly the potentially life-threatening cardiac events.

Aspects of the present invention are also particularly useful for studying the effects of vagus nerve stimulation. Little is known about why vagus nerve stimulation is effective in treating epilepsy and depression. Optogenetic techniques provide a means of studying and improving these treatments. In animal models, ChR2 expression in various types of vagal fibers allows for the identification of the specific fibers best suited for stimulation. Once these fibers of interest are identified, therapies could be modulated so that only these fibers are stimulated, thus avoiding unwanted side effects.

In certain embodiments, inhibition is desired, rather than stimulation. Vagus nerve techniques for appetite suppression involve either severing the nerve or over-stimulating it so that it no longer has meaningful effect on the gastrointestinal system. However, damage to the vagus nerve can cause gastroparesis, where the stomach no longer propels food forward through the digestive system, causing nausea, vomiting, and dangerous fluctuations in blood sugar levels.

In one such embodiment, NpHR is used to provide a more targeted technique to depress vagus nerve firing. The optical stimulation of the NpHR can be provided to specific times, such as during meals, to more closely mimic natural physiology. For example, optical stimulation could be responsive to patient input indicating consumption of food. Alternately, one could bypass the vagus nerve and instead express ChR2 in the muscles of the proximal stomach. These muscles relax to allow the stomach to expand while eating; blocking or mitigating this expansion through ChR2 stimulation would create a premature sense of satiety, similar to the effects of gastric bypass surgery. Selection of one treatment method over the other can be determined as a function of the ability to directly control stomach muscle movement against the complexity of needing a light source for the entire stomach muscle region rather than a small cuff for the vagus nerve.

Other aspects of the present invention relate to cardiac applications. Abnormal heart rhythms, such as atrial fibrillation or atrial flutter, are often treated using defibrillation and cardioversion. These treatments are based on the concept of creating a large electrical field to interrupt the abnormal heart rhythms, thereby allowing the heart to return to normal rhythm. This is also the basis for external defibrillation, used to resuscitate patients that otherwise would die using an external shock system. Implantable defibrillators have become the standard of care in patients felt to be at high risk for life-threatening rhythm abnormalities called ventricular tachycardia or ventricular fibrillation. These devices have several major limitations—one of the greatest limitations is the need for a painful shock and potential for symptoms prior to conversion due to the inability of the device to prevent the rhythm from occurring or progressing prior to the shock. The shock is not desirable since it is painful and creates patient anxiety, resulting in an impairment of quality of life.

For atrial arrhythmias such as atrial fibrillation, techniques such as catheter ablation often do not completely eliminate atrial fibrillation. Since there are estimates of millions of patients currently with atrial fibrillation, a substantial numbers of patients may remain in atrial fibrillation. Atrial fibrillation results in an increased risk of stroke in most patients and may be highly symptomatic. For many of these patients, electrical cardioversion is possible but requires anesthesia to be administered with its resulting inconvenience and cost. Implantable defibrillators, although approved for this indication, have not been utilized for atrial fibrillation: the discomfort of the shock is not well tolerated, and only about 50% of atrial fibrillation episodes are converted by maximum energies in current implantable defibrillators.

Consistent with a specific implementation, local activation of cells in specific regions or with specific cell types is used to assess the role of the cells in the genesis of arrhythmias. There are two fundamental mechanisms that might be employed to convert atrial or ventricular arrhythmias. The first mechanism brings localized regions of heart tissue in specific geometric relationships to reach subthreshold potential so that the abnormal rhythm stops. The second mechanism controls afferent sympathetic and parasympathetic nerves with optical stimulation. In the first mechanism, the subthreshold regions create firewalls around the regions of initiation of the ventricular tachycardia or ventricular fibrillation so that the rhythm would not actually start, while in the second mechanism the vagus nerve itself (for example) can be accessed at a position where the cardiac fibers are still embedded.

Embodiments of the present invention are particularly useful for replacement of supplementation of electrical stimulation therapies that target phrenic and sacral nerves. The phrenic nerve controls the diaphragm, and implantable electrodes can be used as an alternative to mechanical ventilators for long term ventilation-support needs. Because the phrenic nerve is relatively isolated and has few functions beyond diaphragm control, electrical stimulation is generally an effective technique. Side effects, however, come from the initial surgery to implant the electrodes, which may include thoracotomy. There is also report of chest pain with stimulation at high intensity, due to simultaneous stimulation of phrenic nerve afferent fibers, though this is generally fixed by lowering the stimulation levels.

Optogenetic techniques can be useful for avoiding the need for thoracotomy to implant the electrodes. With the specificity provided by genetic targeting, accidental stimulation of unwanted nerves can be mitigated or completely prevented. Therefore an LED cuff (or alternate light source) could be installed above the rib cage, where the nerve first leaves the spinal cord. This would avoid the need for a potentially dangerous thoracotomy, and would hasten postoperative recovery time.

The sacral nerve influences bladder and bowel control, and may be damaged either in paraplegia, or as a side effect of radical prostatectomy. Correct bladder control is the product of careful coordination of the detrusor and sphincter muscles, as controlled by sacral nerve parasympathetics and thoracic nerve sympathetics. While filling, the sphincter muscles must remain strongly activated, while the detrusor muscles relax to allow the bladder to stretch, as monitored by stretch receptors. Bladder release requires coordination of these same muscles in the opposite fashion: sphincter muscles release followed by detrusor muscle contraction. Failure to synchronize these events is known as detrusor-sphincter dysenergia (DSD).

Electrical stimulation suppresses hyperreflexia of the detrusor muscle, allowing for increased bladder filling and increased time between voiding, however DSD is sometimes a side effect of stimulation. Alternately, dorsal rhizotomy is sometimes performed to increase bladder capacity and provide urinary continence. However, both of these techniques are clearly limited; one can either stimulate or cut innervation, but not do both in carefully timed succession as would be needed for true restoration of function. With the genetic targeting techniques, and light cuffs implanted around the sacral and thoracic nerves, optogenetic techniques allow control of the sphincter and detrusor muscles, so that stimulation and inhibition of each could be achieved with high synchrony, effectively recreating normal bladder physiology.

Other embodiments of the present invention relate to uses of stem cells. The success of bone marrow transplantation demonstrates the great promise of stem cell research. However, in many areas of stem cell research, potential therapies still face major technical hurdles. While injected stem cells will often successfully repopulate cells in the needed area, it is difficult to guarantee that these new cells will perform the needed function.

One promising field of research is the use of skeletal myoblasts and stem cells to treat myocardial infarctions and heart failure. Intravenous injection of these cells does improve cardiac function, but there is significant concern that the treatment may be arrythmogenic, either because of the electrical properties of the injected cells, or because of damage or increased nerve sprouting from the injection.

A second major research area is the use of stem cell injections to treat spinal cord injury. Here it is difficult to establish what types of cells are most appropriate in order to bridge the injured area and to restore function. A cell that is less differentiated has more potential to react to the environmental cues to produce the needed variety of cells; however, it also has more potential to differentiate to produce unwanted cell types, creating the danger of teratomas and other cancerous growths. Also, even once the cells are in place, they may or may not integrate into the neural circuit and become functional.

Optogenetic techniques can be used to solve some of the problems faced by stem cell therapies, particularly in cases such as the cardiac, muscular, and nervous systems, where the cells need to perform specific electrical tasks. Stem cells are often genetically modified prior to injection; the inclusion of ChR2 and NpHR would allow direct control of the electrical properties of the transplanted cells, insuring that cells will be functional.

In the case of myocardial repair, tonic NpHR inhibition could be used to prevent arrhythmia, as discussed previously. A detector noting changes in the potential fields around cardiac pacemaker cells could trigger stimulating light pulses, so that the new cells would fire in synchrony with the native myocardial cells.

With spinal cord injury, it may be possible to use optogenetically modified stem cells directly at the site of injury. Knowledge of the complex circuitry can be used to determine and provide the needed light stimulation patterns. An alternative implementation uses modified skeletal muscle stem cells ("satellite cells") to repopulate muscles with cells that are responsive to optical control. For example, after spinal cord or nerve injury, denervated muscle begins to atrophy from lack of use. Rather than attempt to reinstitute peripheral nerve supply, one could use optical stimulation to control a newly grown population of skeletal muscle cells.

Muscle fibers evolve and change type from slow to fast twitch and the reverse, according to patterns of stimulation. Accordingly coordination of stimulation patterns to specific muscle types is implemented. Establishment of different populations of satellite cells that respond to different frequencies of light allows for independent control of slow and fast twitch muscle fibers.

For the various embodiments of the present invention discussed herein, one concern is the ability to effectively use gene therapy without significant side-effects. Animal studies have thus far shown that the expression of these types of foreign proteins in neuron cell membranes does cause an immune response. Notwithstanding, inflammatory effects can be countered using oral peptide-tolerization strategies or mild oral immunosuppression strategies, which can specifically reduce inflammatory responses. Further advances in gene therapy and immune suppression techniques will help to minimize these risks.

Moreover, these types of side-effects are relatively minor when compared to many of the severe ailments that can be treated, such as for intense chronic pain and severe cardiac arrhythmias. With progressively safer genetic techniques, the therapies proposed herein become increasingly viable, and optogenetic therapies may be the preferred approach even when they offer only slight benefits over traditional techniques.

The invasiveness of implantation surgery, scarring around electrodes or light sources, longevity of electronics and power supplies, and battery requirements in the case of power supply implantation, or possible infection risks if wire leads are needed to connect to a power supply outside the body can be mitigated using biocompatible materials and/or power supplies.

While the present invention has been described above, the skilled in the artisan will recognize that many changes may be made thereto without departing from the spirit and scope of the present invention. Such changes may include, for example, the implementation of one or more approaches involving variations of optically responsive ion channels. These and other approaches as described in the contemplated claims below characterize aspects of the present invention.

What is claimed is:

1. A system for stimulating motor units, the system comprising:
   a) a light generator comprising one or more light sources;
   b) a control unit that controls the one or more light sources and modifies properties of light produced by the one or more light sources, wherein the control unit comprises a stimulus profile comprising a variation of optical intensities from the one or more light sources configured to selectively modulate the activity of the motor units as a function of a recruitment order of the motor units that correspond to motor units of different physical sizes, contraction strengths, and motor axon conduction latency;
   c) a motor unit monitor that provides feedback on activation and/or inhibition of motor units by the light; and
   d) a delivery component comprising one or more nucleic acids comprising nucleotide sequences encoding an excitation light-responsive opsin polypeptide and/or an inhibitory light-responsive opsin polypeptide, wherein motor neurons of the motor units express the excitation light-responsive opsin polypeptide and/or the inhibitory light-responsive opsin polypeptide that are activated in response to the light from the one or more light sources, wherein the number of light-responsive opsin polypeptides that are activated increases as the optical intensity of light increases, and wherein the number of light-responsive opsin polypeptides that are activated per motor axon volume of the motor neurons in response to light decreases as the volume of motor axons of the motor neurons increases.

2. The system of claim 1, wherein the control unit comprises one or more of a rectifier circuit, a battery, an integrated circuit, a pulse timer, and a comparator circuit.

3. The system of claim 1, wherein the control unit generates the stimulus profile to control the light generator.

4. The system of claim 3, further comprising a stimulation profile database, wherein the stimulus profile is stored in the stimulation profile database.

5. The system of claim 1, further comprising a results database for storing information relating to the activation of motor units by light.

6. The system of claim 1, wherein the light source is a light-emitting diode.

7. The system of claim 1, comprising one or more parameter controls that control the one or more light sources by modifying the light properties.

8. The system of claim 7, wherein the light properties include wavelength and intensity.

9. The system of claim 1, wherein at least a portion of the system is implantable.

10. The system of claim 1, wherein the excitation light-responsive opsin polypeptide is a ChR2 polypeptide.

11. The system of claim 1, wherein the inhibitory light-responsive opsin polypeptide is an NpHR polypeptide.

12. The system of claim 1, wherein the nucleotide sequences are operably linked to a promoter.

13. The system of claim 1, wherein the delivery component comprises two nucleic acids, wherein the first nucleic acid comprises the nucleotide sequence encoding the excitation light-responsive opsin polypeptide and the second nucleic acid comprises the nucleotide sequence encoding the inhibitory light-responsive opsin polypeptide, wherein said delivery component facilitates targeted expression of both the nucleic acid encoding the excitation light-responsive opsin polypeptide and the nucleic acid encoding the inhibitory light-responsive opsin polypeptide.

14. The system of claim 1, wherein the stimulus profile is set according to a muscle fatigue factor.

15. The system of claim 1, wherein the system is configured to provide graduated levels of optical stimulation from the one or more light sources as a function of a ratio of fast to slow twitch motor neurons of the motor units.

16. The system of claim 1, wherein the stimulus profile further comprises a variation in optical frequency or spatial location of light from the one or more light sources.

* * * * *